US007879811B2

(12) United States Patent
Green et al.

(10) Patent No.: US 7,879,811 B2
(45) Date of Patent: *Feb. 1, 2011

(54) FORMULATIONS COMPRISING ANTISENSE NUCLEOTIDES TO CONNEXINS

(75) Inventors: Richard Colin Green, Auckland (NZ); David Laurence Becker, Langley (NZ)

(73) Assignee: Coda Therapeutics, Inc., San Diego, CA (US)

( * ) Notice: Subject to any disclaimer, the term of this patent is extended or adjusted under 35 U.S.C. 154(b) by 597 days.

This patent is subject to a terminal disclaimer.

(21) Appl. No.: 11/510,498

(22) Filed: Aug. 25, 2006

(65) Prior Publication Data

US 2008/0221051 A1 Sep. 11, 2008

Related U.S. Application Data

(63) Continuation of application No. 09/890,363, filed as application No. PCT/GB00/00238 on Jan. 27, 2000, now Pat. No. 7,098,190.

(30) Foreign Application Priority Data

Jan. 27, 1999 (NZ) ........................ 333928
Oct. 7, 1999 (NZ) ........................ 500190

(51) Int. Cl.
*A61K 31/70* (2006.01)
*C07H 21/02* (2006.01)
*C07H 21/04* (2006.01)
*C12Q 1/68* (2006.01)

(52) U.S. Cl. .......................... 514/44 A; 435/6; 435/375; 435/377; 536/23.1; 536/24.1; 536/25.5

(58) Field of Classification Search ........................ None
See application file for complete search history.

(56) References Cited

FOREIGN PATENT DOCUMENTS

WO WO9619194 6/1996
WO WO9824797 6/1998

OTHER PUBLICATIONS

Agrawal, S., TIBTECH vol. 14:376-387 Oct. 1996.
Branch, A., TIBS vol. 23:45-50, Feb. 1998.
Jen et al., Stem Cells, vol. 18:307-319, 2000.
Qiu et al., Current Biology, vol. 13:1697-1703, Sep. 30, 2004.
Hodgins, M., Journal of Investigative Dermatology, vol. 122(5):ix-x, 2004.
Ruch, R. et al., Molecular Carcinogenesis 14:269-274, 1995.
Goliger, J. et al., Molecular Biology of the Cell 6:1491-1501, 1995.
Moore et al., Am J. Physiology, vol. 265, No. 1, pp. C1371-C1388, 1994.
European Patent Office, Search Report for Application No. 05016736.0, Dec. 19, 2005.
Grazul-Bilska et al., Abstract, Biology Reproduction, vol. 58, No. 1, p. 78, 1998.
Davis et al., "Modulation of Connexin43 Expression: Effects on Cellular Coupling", Journal of Cardiovascular Electrophysiology, 1995.
Rozenthal et al., "Stable Transfection with Connexin43 Inhibits Neuronal Differentiation of PC12 Cells", Oct. 25, 1997, U.S.
Becker et al., "Connexin Alpha1 and Cell Proliferation in the Developing Chick Retina" Experimental Neurology, vol. 156, No. 2, Apr. 1999, pp. 326-332, XP002347187 ISSN: 0014-4886.
Green et al., "Spatiotemporal Depletion of Connexins Using Antisense Oligonucleotides." Methods in Molecular Biology (Clifton, N.J.) 2001, vol. 154, 2001, pp. 175-185, XP008053224 ISSN: 1064-3745.
Franteseva, M. et al., "Ischemia-Induced Brain Damage Depends on Specific Gap-Junctional Coupling" Journal of Cerebral Blood Flow and Metabolism, vol. 22, No. 4, Apr. 2002, pp. 453-462, XP008053227 ISSN: 0271-678X.
Ratkay-Traub et al., "Regeneration of Rabbit Cornea Following Excimer Laser Photorefractive Keratectomy: A Study on Gap Junctions, Epithelial Junctions and Epidermal Growth Factor Receptor Expression in Correlation with Cell Proliferation", Experimental Eye Research, vol. 73, No. 3, Sep. 2001, pp. 291-302, XP002347188 ISSN: 0014-4835.
Baldwin, H. et al., "Growth Factors in Corneal Wound Healing Following Refractive Surgery: A Review" Acta Opthalmologica Scandinavica, vol. 80, No. 3, Jun. 2002, pp. 238-247, XP002347189 ISSN:1395-3907.
Willecke, K. et al "Structural and Functional Diversity of Connexin Genes in the Mouse and Human Genome" Biological Chemistry, vol. 383, No. 5, May 2002, pp. 725-737, XP008053223 ISSN: 1431-6730.
Santoro, S. et al., "A General Purpose RNA-Cleaving DNA Enzyme" Proceedings of the National Academy of Sciences USA, vol. 94, Apr. 1997, pp. 4262-4266, XP001009844 ISSN: 0027-8424.

*Primary Examiner*—Sean R McGarry
(74) *Attorney, Agent, or Firm*—Duane Morris LLP

(57) ABSTRACT

A therapeutic and/or cosmetic formulation comprising at least one anti-sense polynucleotide to a connexin protein together with a pharmaceutically acceptable carrier or vehicle is useful in site specific down regulation of connexin protein expression, particularly in reduction of neuronal cells death, wound healing, reduction of inflammation, decrease of scar formation and skin rejuvenation and thickening.

153 Claims, 18 Drawing Sheets

SEQUENCE LISTING

<160> NUMBER OF SEQ ID NOS: 12

<210> SEQ ID NO 1
<211> LENGTH: 30
<212> TYPE: DNA
<213> ORGANISM: Artificial
<220> FEATURE:
<223> OTHER INFORMATION: oligonucleotide

<400> SEQUENCE: 1
gtaattgcgg caagaagaat tgtttctgtc        30

<210> SEQ ID NO 2
<211> LENGTH: 30
<212> TYPE: DNA
<213> ORGANISM: Artificial
<220> FEATURE:
<223> OTHER INFORMATION: Oligonucleotide -continued

```
<400> SEQUENCE: 2
gtaattgcgg caggaggaat tgtttctgtc                                30

<210> SEQ ID NO 3
<211> LENGTH: 30
<212> TYPE: DNA
<213> ORGANISM: Artificial
<220> FEATURE:
<223> OTHER INFORMATION: Oligonucleotide

<400> SEQUENCE: 3
ggcaagagac accaaagaca ctaccagcat                                30

<210> SEQ ID NO 4
<211> LENGTH: 27
<212> TYPE: DNA
<213> ORGANISM: Artificial
<220> FEATURE:
<223> OTHER INFORMATION: Oligonucleotide

<400> SEQUENCE: 4
tcctgagcaa tacctaacga acaaata                                   27

<210> SEQ ID NO 5
<211> LENGTH: 25
<212> TYPE: DNA
<213> ORGANISM: Artificial
<220> FEATURE:
<223> OTHER INFORMATION: Oligonucleotide

<400> SEQUENCE: 5
cgtccgagcc cagaaagatg aggtc                                     25

<210> SEQ ID NO 6
<211> LENGTH: 25
<212> TYPE: DNA
<213> ORGANISM: Artificial
<220> FEATURE:
<223> OTHER INFORMATION: Oligonucleotide

<400> SEQUENCE: 6 tttctttttct atgtgctgtt ggtga                                    25

<210> SEQ ID NO 7
<211> LENGTH: 30
<212> TYPE: DNA
<213> ORGANISM: Artificial
<220> FEATURE:
<223> OTHER INFORMATION: oligonucleotide

<400> SEQUENCE: 7
gacagaaaca attcctcctg ccgcaattac                                30

<210> SEQ ID NO 8
<211> LENGTH: 30
<212> TYPE: DNA
<213> ORGANISM: Artificial
<220> FEATURE:
<223> OTHER INFORMATION: Oligonucleotide

<400> SEQUENCE: 8
gtagttacga caggaggaat tgttctcgtc                                30

<210> SEQ ID NO 9
```

```
<211> LENGTH: 30
<212> TYPE: DNA
<213> ORGANISM: Artificial
<220> FEATURE:
<223> OTHER INFORMATION: Oligonucleotide

<400> SEQUENCE: 9
tcgaactgtc aagactgcta tggcgatcat                                      30

<210> SEQ ID NO 10
<211> LENGTH: 28
<212> TYPE: DNA
<213> ORGANISM: Artificial
<220> FEATURE:
<223> OTHER INFORMATION: Oligonucleotide

<400> SEQUENCE: 10
ttgtgattta tttagttcgt ctgatttc                                        28

<210> SEQ ID NO 11
<211> LENGTH: 30
<212> TYPE: DNA
<213> ORGANISM: Artificial
<220> FEATURE:
<223> OTHER INFORMATION: Oligonucleotide

<400> SEQUENCE: 11
gacagaaaca attcctcctg ccgcaattac                                      30

<210> SEQ ID NO 12
<211> LENGTH: 1149
<212> TYPE: DNA
<213> ORGANISM: Homo sapiens

<400> SEQUENCE: 12
atgggtgact ggagcgcctt aggcaaactc cttgacaagg ttcaagccta ctcaactgct     60
ggagggaagg tgtggctgtc agtactttc attttccgaa tcctgctgct ggggacagcg    120
gttgagtcag cctggggaga tgagcagtct gcctttcgtt gtaacactca gcaacctggt    180
tgtgaaaatg tctgctatga caagtctttc ccaatctctc atgtgcgctt ctgggtcctg    240
cagatcatat ttgtgtctgt acccacactc ttgtacctgg ctcatgtgtt ctatgtgatg    300
cgaaaggaag agaaactgaa caagaaagag gaagaactca aggttgccca aactgatggt    360
gtcaatgtgg acatgcactt gaagcagatt gagataaaga gttcaagta cggtattgaa    420 gagcatggta aggtgaaaat gcgaggggggg ttgctgcgaa cctacatcat cagtatcctc    480
ttcaagtcta tctttgaggt ggccttcttg ctgatccagt ggtacatcta tggattcagc    540
ttgagtgctg tttacacttg caaaagagat ccctgcccac atcaggtgga ctgtttcctc    600
tctcgcccca cggagaaaac catcttcatc atcttcatgc tggtggtgtc cttggtgtcc    660
ctggccttga atatcattga actcttctat gttttcttca agggcgttaa ggatcgggtt    720
aagggaaaga gcgaccctta ccatgcgacc agtggtgcgc tgagccctgc caaagactgt    780
gggtctcaaa aatatgctta tttcaatggc tgctcctcac caaccgctcc cctctcgcct    840
atgtctcctc ctgggtacaa gctggttact ggcgacagaa acaattcttc ttgccgcaat    900
tacaacaagc aagcaagtga gcaaaactgg gctaattaca gtgcagaaca aaatcgaatg    960
gggcaggcgg gaagcaccat ctctaactcc catgcacagc cttttgattt ccccgatgat   1020
```

```
aaccagaatt  ctaaaaaact  agctgctgga  catgaattac  agccactagc  cattgtggac      1080
cagcgacctt  caagcagagc  cagcagtcgt  gccagcagca  gacctcggcc  tgatgacctg      1140
gagatctag                                                                  1149
```

US 7,879,811 B2

FORMULATIONS COMPRISING ANTISENSE NUCLEOTIDES TO CONNEXINS

CROSS-REFERENCE TO RELATED APPLICATIONS

This application is a continuation of U.S. application Ser. No. 09/890,363, filed Nov. 2, 2001 (now issued as U.S. Pat. No. 7,098,190), which is a U.S. National Stage Application of International PCT Application No. PCT/GB00/00238, filed Jan. 27, 2000 (published as WO00/44409 on Aug. 3, 2000) and claims the benefit of priority to NZ 333928 (filed Jan. 27, 1999) and NZ 500190 (filed Oct. 7, 1999). The contents of each of which are hereby incorporated in their entireties.

FIELD

This invention relates to formulations for use in therapeutic and/or cosmetic treatments, particularly those in which a localised disruption in direct cell-cell communication is desirable.

BACKGROUND

Gap junctions are cell membrane structures which facilitate direct cell-cell communication. A gap junction channel is formed of two hemichannels (connexons), each composed of six connexin subunits. These connexins are a family of proteins, commonly named according to their molecular weight or classified on a phylogenetic basis ie. into an α class and a β class.

An ability to control connexin expression (and in particular to downregulate it) would therefore provide an opportunity to modulate cell-cell communication within a patient for therapeutic and/or remedial purposes. However, as a number of connexin proteins are expressed widely throughout the body, a general downregulatory effect is undesirable in inducing a therapeutic effect at a specific site.

Anti-sense oligodeoxynucleotides (ODN's) have considerable potential as agents for the manipulation of specific gene expression (reviewed: Stein et al., 1992; Wagner 1994). However, there remain difficulties which need to be overcome. These include the short half life of such ODN's (unmodified phosphodiester oligomers typically have an intracellular half life of only 20 minutes owing to intracellular nuclease degradation (Wagner 1994)) and their delivery consistently and reliably to target tissues.

It was with the intent of at least partially overcoming these difficulties that the applicants devised the present invention.

SUMMARY OF THE INVENTION

Accordingly, in a first aspect, the invention provides a formulation for use in therapeutic and/or cosmetic treatment, which formulation comprises:

at least one anti-sense polynucleotide to a connexin protein; together with a pharmaceutically acceptable carrier or vehicle.

In one preferred form, the formulation contains polynucleotides to one connexin protein only. Most preferably, this connexin protein is connexin 43.

Many aspects of the invention are described with reference to oligodeoxynucleotides. However it is understood that other suitable polynucleotides (such as RNA polynucleotides) may be used in these aspects.

Alternatively, the formulation contains oligodeoxynucleotides to more than one connexin protein. Preferably, one of the connexin proteins to which oligodeoxynucleotides are directed is connexin 43. Other connexin proteins to which oligodeoxynucleotides are directed include connexin 26, connexin 31.1 and connexin 32.

Conveniently, the oligodeoxynucleotide to connexin 43 is selected from:

```
                                      (SEQ ID NO: 1)
    GTA ATT GCG GCA AGA AGA ATT GTT TCT GTC;

(SEQ ID NO: 2)
    GTA ATT GCG GCA GGA GGA ATT GTT TCT GTC;
    and (SEQ ID NO: 3)
    GGC AAG AGA CAC CAA AGA CAC TAC CAG CAT
```

Most conveniently, the oligodeoxynucleotide to connexin 43 is:

```
                                      (SEQ ID NO: 1)
    GTA ATT GCG GCA AGA AGA ATT GTT TCT GTC.
```

Conveniently, the oligodeoxynucleotide to connexin 26 is:

```
TCC TGA GCA ATA CCT AAC GAA CAA ATA. (SEQ ID NO: 4)
```

Conveniently, the oligodeoxynucleotide to connexin 31.1 is:

```
CGT CCG AGC CCA GAA AGA TGA GGT C. (SEQ ID NO: 5)
```

Conveniently, the oligodeoxynucleotide to connexin 32 is:

```
TTT CTT TTC TAT GTG CTG TTG GTG A. (SEQ ID NO: 6)
```

The anti-sense polynucleotides may be formulated for parenteral, intramuscular, intracerebral, intravenous, subcutaneous or transdermal administration. The antisense polynucleotides are preferably administered topically (at the site to be treated). Suitably the antisense polynucleotides are combined with a pharmaceutically acceptable carrier, vehicle or diluent to provide a pharmaceutical composition.

Suitable pharmaceutically acceptable carriers or vehicles include any of those commonly used for topical administration. The topical formulation may be in the form of a cream, ointment, gel, emulsion, lotion or paint. The formulation of the invention may also be presented in the form of an impregnated dressing.

Suitable carrier materials include any carrier or vehicle commonly used as a base for creams, lotions, gels, emulsions, lotions or paints for topical administration. Examples include emulsifying agents, inert carriers including hydrocarbon bases, emulsifying bases, non-toxic solvents or water-soluble bases. Particularly suitable examples include lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol and stearyl alcohol.

Preferably, the pharmaceutically acceptable carrier or vehicle is a gel, suitably a nonionic polyoxyethylene-polyoxypropylene copolymer gel, for example, a Pluronic gel, preferably Pluronic F-127 (BASF Corp.). This gel is particularly preferred as it is a liquid at low temperatures but rapidly sets at physiological temperatures, which confines the release of the ODN component to the site of application or immediately adjacent that site.

An auxiliary agent such as casein, gelatin, albumin, glue, sodium alginate, carboxymethylcellulose, methylcellulose, hydroxyethylcellulose or polyvinyl alcohol may also be included in the formulation of the invention.

The pharmaceutical composition may be formulated to provide sustained release of the antisense polynucleotide.

Conveniently, the formulation further includes a surfactant to assist with oligodeoxynucleotide cell penetration or the formulation may contain any suitable loading agent. Any suitable non-toxic surfactant may be included, such as DMSO. Alternatively a transdermal penetration agent such as urea may be included.

In a further aspect, the invention provides a method of site-specific downregulation of connexin protein expression for a therapeutic and/or cosmetic purpose which comprises administering a formulation as defined above to a site on or within a patient at which said downregulation is required.

In still a further aspect, the invention provides a method of reducing neuronal cell death which would otherwise result from a neuronal insult to a specific site in the brain, spinal cord or optic nerve of a patient which comprises the step of administering a formulation as defined above to said site to downregulate expression of connexin protein(s) at and immediately adjacent said site.

Preferably, the formulation is administered to reduce neuronal loss due to physical trauma to the brain, spinal cord or optic nerve.

Conveniently, the formulation is administered in a sufficient amount to down-regulate expression of said connexin protein(s) for at least 24 hours postadministration.

In yet a further aspect, the invention provides a method of promoting wound healing in a patient which comprises the step of administering a formulation as defined above to said wound to downregulate expression of connexin protein(s) at and immediately adjacent the site of said wound.

Usually, the wound will be the result of trauma, including burns. It may however be the result of surgery.

In yet a further aspect, the invention provides a method of reducing inflammation as part of treating a wound and/or tissue subjected to physical trauma which comprises the step of administering a formulation as defined above to or proximate to said wound or tissue.

Preferably, said wound is a burn.

Alternatively, said wound is the result of physical trauma to tissue, including neuronal tissue such as the brain, spinal cord or optic nerve.

In yet a further aspect, the invention provides a method of decreasing scar formation in a patient who has suffered a wound which comprises the step of administering a formulation as defined above to said wound to downregulate expression of connexin protein(s) at and immediately adjacent the site of said wound.

Again, the wound may be the result of trauma or surgery, with the formulation being applied to the wound immediately prior to surgical repair and/or closure thereof.

In yet a further aspect, the invention provides a method of skin rejuvenation or thickening for a cosmetic or therapeutic purpose which comprises the step of administering, once or repeatedly, a formulation as defined above to the skin surface.

Conveniently, said formulation includes oligodeoxynucleotides directed to connexin 26 or connexin 43 and is administered to regulate epithelial basal cell division and growth.

In another embodiment, said formulation includes oligodeoxynucleotides directed to connexin 31.1 and is administered to regulate outer layer keratinisation.

Preferably, the formulation is a cream or gel.

DESCRIPTION OF THE DRAWINGS

FIGS. 1 to 5 show sections of rat brain lesions treated with Pluronic gel containing antisense oligodeoxynucleotides specific to connexin 43, or for control lesions, Pluronic gel alone. In all cases lesions were sectioned serially in a coronal plane and the mid point sections used for analysis. Each image (except FIG. 5) shows 4 mm by 5.33 mm of tissue. FIG. 5 is approximately 1.2 mm by 2 mm.

FIG. 1.

FIG. 2: A control lesion 24 hours after wounding.

FIG. 3: FIG. 3A has been stained for Nissl (blue nuclei) and Neuronal-N (pink cells). Note how compact the lesion is, even after 48 hours, compared with control lesions (FIGS. 1 and 2). While there is some spread to the right hand side, the left side of the lesion essentially follows the original needle tract with little sign of spreading. The left side of the lesion is very straight and it has not spread down to the corpus callosum.

FIG. 4.

FIG. 5: A higher magnification view showing the edge of a connexin 43 antisense treated lesion. The edge of the lesion has been marked showing viable neurons (Neuronal-N labelled) right up to the edge of the wounding needle tract even 48 hours after lesioning.

DESCRIPTION OF THE INVENTION

Figure 1A:
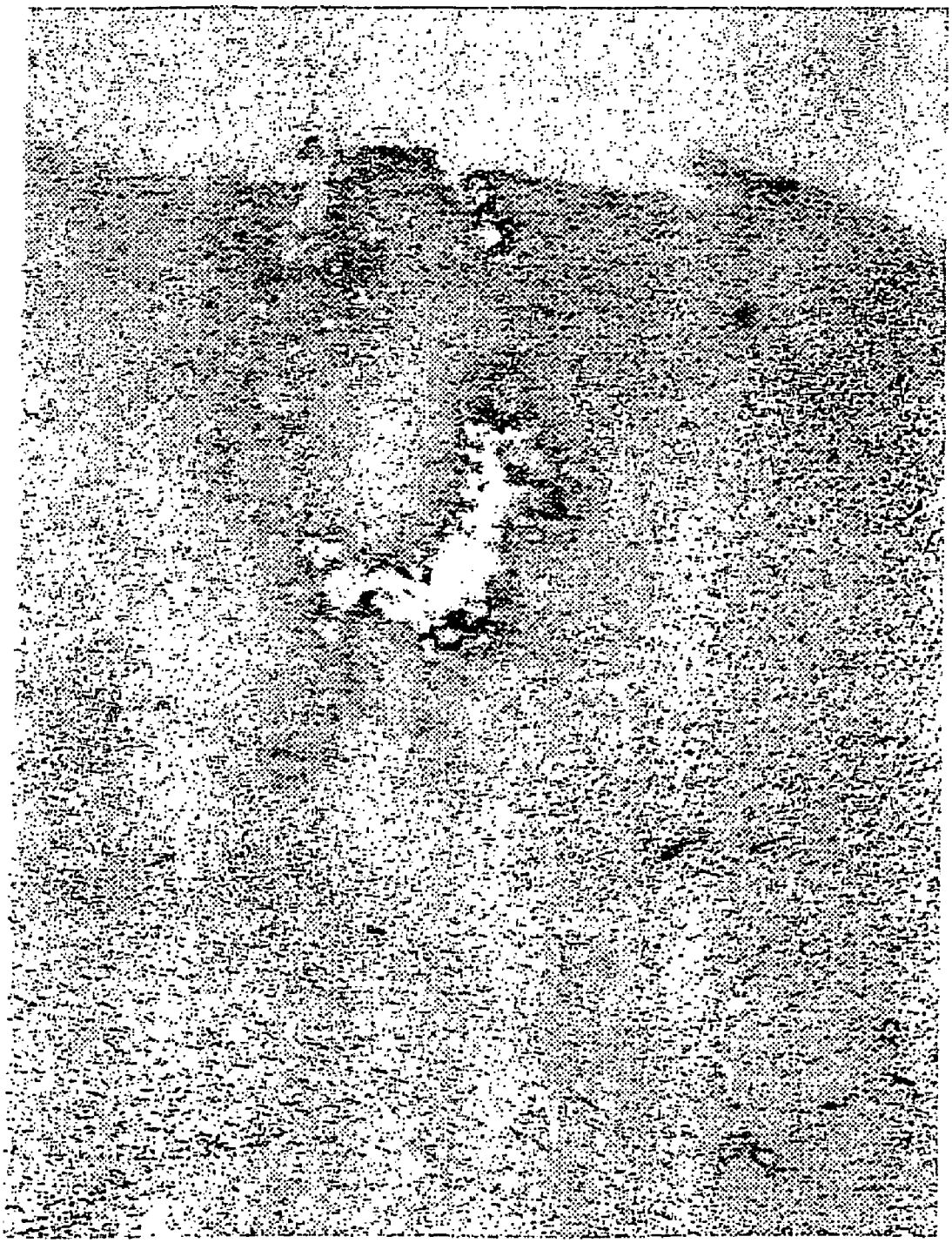
FIGS. 1A and 1C show two side of a control lesion 24 hours after lesioning. The lesion has been treated with Pluronic gel alone. The sections have been Nissl stained (blue nuclei) and antibody labelled with the neuronal marker Neuronal-N (brown cells).
Figure 1B:
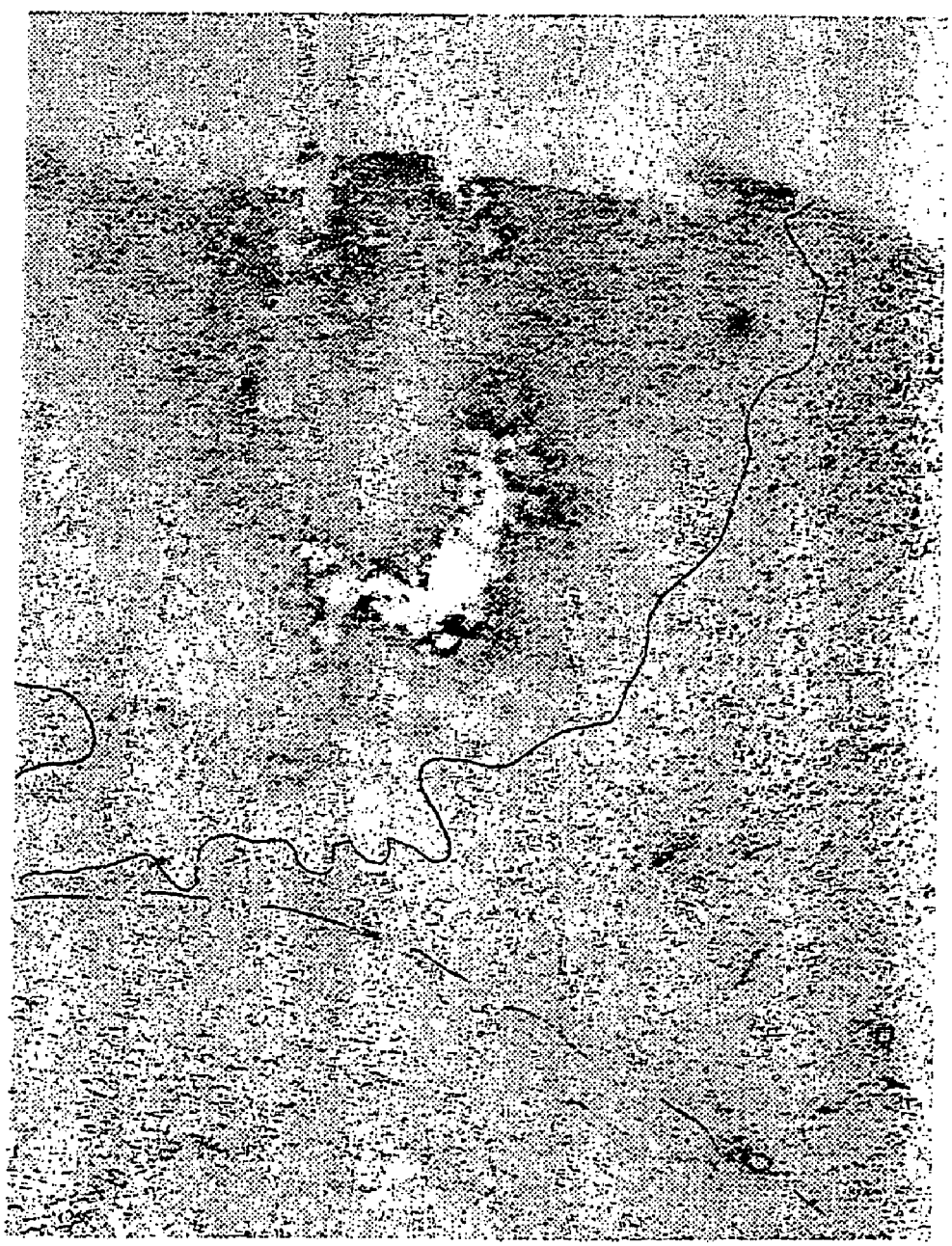
FIGS. 1B and 1D show grey scale images of 1A and 1C respectively with the outline of the lesion marked. Note the large size of the lesion and the irregular spreading edges. The lesion has spread downwards toward the corpus callosum (dashed line) within just 24 hours of lesioning.
Figure 1C:
Figure 1D:
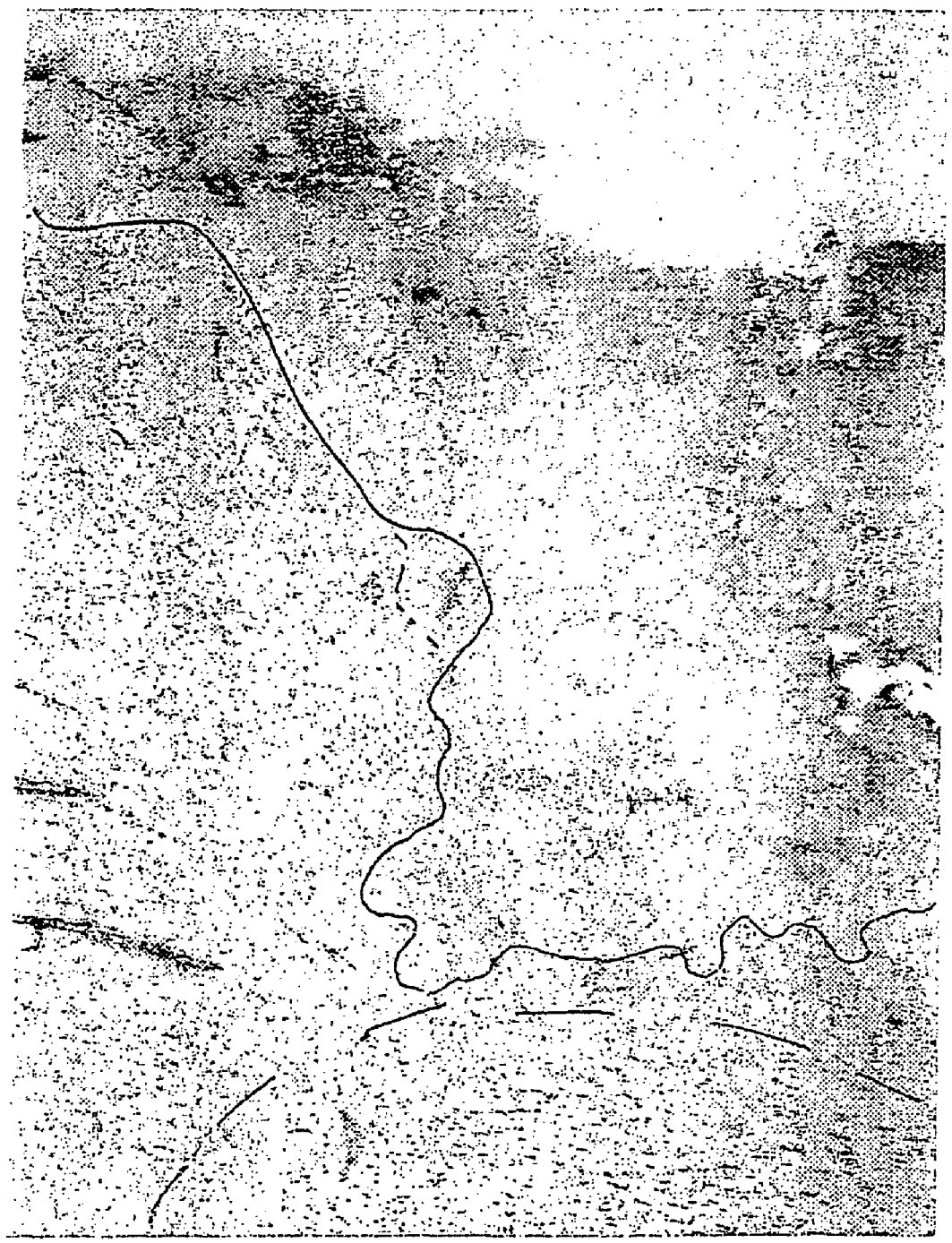

As broadly defined above, the focus of the invention is on site-specific downregulation of connexin expression. This will have the effect of reducing direct cell-cell communication at the site at which connexin expression is downregulated, which gives rise to numerous therapeutic/cosmetic applications as described below.

The downregulation of connexin expression is based generally upon the anti-sense approach using antisense polynucleotides (such as DNA or RNA polynucleotides), and more particularly upon the use of antisense oligodeoxynucleotides (ODN). These polynucleotides (eg. ODN) target the connexin protein (s) to be downregulated. Typically the polynucleotides are single stranded, but may be double stranded.

The antisense polynucleotide may inhibit transcription and/or translation of the connexin. Preferably the polynucleotide is a specific inhibitor of transcription and/or translation from the connexin gene, and does not inhibit transcription and/or translation from other genes. The product may bind to the connexin gene or mRNA either (i) 5' to the coding sequence, and/or (ii) to the coding sequence, and/or (iii) 3' to the coding sequence.

Generally the antisense polynucleotide will cause the expression of connexin mRNA and/or protein in a cell to be reduced.

The antisense polynucleotide is generally antisense to the connexin mRNA. Such a polynucleotide may be capable of hybridising to the connexin mRNA and may thus inhibit the expression of connexin by interfering with one or more aspects of connexin mRNA metabolism including transcription, mRNA processing, mRNA transport from the nucleus, translation ormRNA degradation. The antisense polynucleotide typically hybridises to the connexin mRNA to form a duplex which can cause direct inhibition of translation and/or destabilisation of the mRNA. Such a duplex may be susceptible to degradation by nucleases.

The antisense polynucleotide may hybridize to all or part of the connexin mRNA. Typically the antisense polynucleotide hybridizes to the ribosome binding region or the coding region of the connexin mRNA. The polynucleotide may be complementary to all of or a region of the connexin mRNA. For example, the polynucleotide may be the exact complement of all or a part of connexin mRNA. However, absolute complementarity is not required and polynucleotides which have sufficient complementarity to form a duplex having a melting temperature of greater than 20° C., 30° C. or 40° C. under physiological conditions are particularly suitable for use in the present invention.

Thus the polynucleotide is typically a homologue of the mRNA. The polynucleotide may be a polynucleotide which hybridises to the connexin mRNA under conditions of medium to high stringency such as 0.03M sodium chloride and 0.03M sodium citrate at from about 50 to about 60 degrees centigrade.

The polynucleotide will typically be from 6 to 40 nucleotides in length. Preferably it will be from 12 to 20 nucleotides in length. The polynucleotides may be at least 40, for example at least 60 or at least 80, nucleotides in length and up to 100, 200, 300, 400, 500, 1000, 2000 or 3000 or more nucleotides in length.

The connexin protein or proteins targeted by the ODN will be dependent upon the site at which downregulation is to be effected. This reflects the nonuniform make-up of gap junction(s) at different sites throughout the body in terms of connexin sub-unit composition. The connexin may be any connexin that naturally occurs in a human or animal. The connexin gene (including coding sequence) generally has homologue with any of the specific connexins mentioned herein, such as homology with the connexin 43 coding sequence shown in Table 3 The connexin is typically an α or β connexin. Preferably the connexin is expressed in the skin or nervous tissue (including brain cells).

Some connexin proteins are however more ubiquitous than others in terms of distribution in tissue. One of the most widespread is connexin 43. ODN's targeted to connexin 43 are therefore particularly suitable for use in the present invention.

It is also contemplated that ODN's targeted at separate connexin proteins be used in combination (for example 1, 2, 3, 4 or more different connexins may be targeted). For example, ODN's targeted to connexin 43, and one or more other members of the connexin family (such as connexin 26, 31.1, 32, 36, 40 and 45) can be used in combination.

Individual antisense polynucleotides may be specific to a particular connexin, or may target 1, 2, 3 or more different connexins. Specific polynucleotides will generally target sequences in the connexin gene or mRNA which are not conserved between connexins, whereas non-specific polynucleotides will target conserved sequences.

The ODN's for use in the invention will generally be unmodified phosphodiester oligomers. They will vary in length but with a 30 mer ODN being particularly suitable.

The antisense polynucleotides may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates.

Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides.

The precise sequence of the antisense polynucleotide used in the invention will depend upon the target connexin protein. For connexin 43, the applicant's have found ODN's having the following sequences to be particularly suitable:

```
                                          (SEQ ID NO: 1)
    GTA ATT GCG GCA AGA AGA ATT GTT TCT GTC;

(SEQ ID NO: 2)
    GTA ATT GCG GCA GGA GGA ATT GTT TCT GTC;
    and (SEQ ID NO: 3)
    GGC AAG AGA CAC CAA AGA CAC TAC CAG CAT
```

ODN's directed to other connexin proteins can be selected in terms of their nucleotide sequence by any convenient, and conventional, approach. For example, the computer programmes MacVector and OligoTech (from Oligos etc. Eugene, Oreg., USA) can be used. For example, ODN's for connexins and 32 have the following sequences:

```
                                          (SEQ ID NO: 4)
    5' TCC TGA GCA ATA CCT AAC GAA CAA ATA
    (connexin 26)

(SEQ ID NO: 5)
    5' CGT CCG AGC CCA GAA AGA TGA GGT C
    (connexin31.1)

(SEQ ID NO: 6)
    5' TTT CTT TTC TAT GTG CTG TTG GTG A (connexin 32)
```

Once selected, the ODN's can be synthesised using a DNA synthesiser.

For use in the invention, the ODN(s) require site-specific delivery. They also require delivery over an extended period of time. While clearly the delivery period will be dependent upon both the site at which the downregulation is to be induced and the therapeutic effect which is desired, continuous delivery for 24 hours or longer will often be required.

In accordance with the present invention, this is achieved by inclusion of the ODN(s) in a formulation together with a pharmaceutically acceptable carrier or vehicle, particularly in the form of a formulation for topical administration.

Once prepared, the formulations of the invention have utility in any therapeutic/cosmetic approach where a transient and site-specific interruption in cell-cell communication is desirable. These include in treating neuronal damage in the brain, spinal cord or optic nerve (where the damage is to be localised as much as possible), in the promotion of wound healing and in reducing scar formation following, for example, cosmetic surgery or burns.

In particular, topical formulations such as creams can be employed to regulate epithelial basal cell division and growth (using ODN's targeted to connexin 43) and outer layer keratinisation (using ODN's targeted to connexin 31.1).

The antisense polynucleotides (including the ODN) may be present in a substantially isolated form. It will be understood that the product may be mixed with carriers or diluents which will not interfere with the intended purpose of the product and still be regarded as substantially isolated. A product of the invention may also be in a substantially purified form, in which case it will generally comprise 90%, e.g. at least 95%, 98% or 99% of the polynucleotide or dry mass of the preparation.

Administration

The antisense polynucleotides (including ODN's) of the invention (typically in the form of the formulation discussed herein) may thus be administered to a human or animal in need of treatment, such as a human or animal with any of the diseases or conditions mentioned herein. The condition of the human or animal can thus be improved. The polynucleotide and formulation may thus be used in the treatment of the human or animal body by therapy. They may be used in the manufacture of a medicament to treat any of the conditions mentioned herein.

The antisense polynucleotides may be administered by typically (at the site to be treated). Preferably the antisense polynucleotides are combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intracerebral, intravenous, subcutaneous, or transdermal administration.

The dose at which an antisense polynucleotide is administered to a patient will depend upon a variety of factors such as the age, weight and general condition of the patient, the condition that is being treated, and the particular antisense polynucleotide that is being administered. A suitable dose may however be from 0.1 to 100 mg/kg body weight such as 1 to 40 mg/kg body weight.

Uptake of nucleic acids by mammalian cells is enhanced by several known transfection techniques for example those including the use of transfection agents. The formulation which is administered may contain such agents. Examples of these agents include cationic agents (for example calcium phosphate and DEAE-dextran) and lipofectants (for example Lipofectam™ and Transfectam™).

The routes of administration and dosages described above are intended only as a guide since a skilled physician will be able to determine readily the optimum route of administration and dosage for any particular patient and condition.

Homologues

Homology and homologues are discussed herein (eg. the polynucleotides may be a homologue of sequence in connexin mRNA). Such polynucleotides typically have at least 70% homology, preferably at least 80, 90%, 95%, 97% or 99% homology with the relevant sequence, for example over a region of at least 15, 20, 40, 100 more contiguous nucleotides (of the homologous sequence).

Homology may be calculated based on any method in the art. For example the UWGCG Package provides the BEST-FIT program which can be used to calculate homology (for example used on its default settings) (Devereux et al (1984) Nucleic Acids Research 12, p 387-395). The PILEUP and BLAST algorithms can be used to calculate homology or line up sequences (typically on their default settings), for example as described in Altschul S. F. (1993) J Mol Evol 36: 290-300; Altschul, S, F et al (1990) J Mol Biol 215: 403-10.

Software for performing BLAST analyses is publicly available through the National Center for Biotechnology Information (http://www.ncbi.nlm.nih.gov/) This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than 0.001.

The homologous sequence typically differs from the relevant sequence by at least (or by no more than) 2, 5, 10, 15, 20 more mutations (which may be substitutions, deletions or insertions). These mutations may be measured across any of the regions mentioned above in relation to calculating homology.

The homologous sequence typically hybridises selectively to the original sequence at a level significantly above background. Selective hybridisation is typically achieved using conditions of medium to high stringency (for example 0.03M sodium chloride and 0.03M sodium citrate at from about 50° C. to about 60° C.). However, such hybridisation may be carried out under any suitable conditions known in the art (see Sambrook et al (1989), Molecular Cloning: A Laboratory Manual). For example, if high stringency is required, suitable conditions include 0.2×SSC at 60° C. If lower stringency is required, suitable conditions include 2×SSC at 60° C.

Various aspects of the invention will now be described with reference to the following experimental section which will be understood to be provided by way of illustration only and not to constitute a limitation on the scope of the invention.

EXPERIMENTAL

Experiment 1

Materials and Methods

Antisense Application

30% Pluronic F-127 gel (BASF Corp) in phosphate buffered saline (molecular grade water) was used to deliver unmodified a1 connexin (connexin 43) specific anti-sense ODN's to the developing chick embryo (Simons, et al., 1992). Chick embryos were incubated at 38° C. and staged according to Hamilton and Hamburger stages. Eggs were windowed and the vitleline and amniotic membranes over the area to be treated were opened using fine forceps. After anti-sense application eggs were sealed with tape and replaced in the incubator for 48 hours at which time most experiments were analysed, the exception being for the time course analysis of a1 connexin "knockdown" and recovery.

Pluronic gel is liquid at low temperatures, 0-4 C, but sets when dropped onto the embryo at physiological temperature, remaining in place for at least 12 hours. The gel has the additional advantage of being a mild surfactant and this, used either alone or in conjunction with DMSO, appeared to markedly expedite ODN penetration into cells (Wagner, 1994). Addition of an FITC tag to DB1 ODN, viewed using confocal laser scanning microscopy, demonstrated intracellular penetration of the probes. Sequences of deoxyoligonucleotides used are shown in Table 1.

TABLE 1

The Effect on Limb Development of ODN
Application Between Stages 8 & 14 of
Chick Embryo Development Antisense oligodeoxynucleotides to Connexin 43

(SEQ ID NO: 2)
DB1 GTA ATT GCG GCA GGA GGA ATT GTT TCT GTC (SEQ ID NO: 3)
CG 1 GGC AAG AGA CAC CAA AGA CAC TAC CAG CAT

Control oligodeoxynucleotides (SEQ ID NO: 7)
DB 1 (sense)
GAC AGA AAC AAT TCC TCC TGC CGC AAT TAC (SEQ ID NO: 8)
DB 1 (chick)
GTA GTT ACG ACA GGA GGA ATT GTT CTC GTC (SEQ ID NO: 9)
CV3 (random)
TCG AAC TGT CAA GAC TGC TAT GGC GAT CAT Gel only All ODN's were applied at 0.5-1.0 µM final concentration following dose dependent analysis during preliminary experiments covering a range of concentrations from 0.05 µM to 50 µM. General toxicity effects only became apparent with ODN concentrations greater than 10 µM. ODN gel mixtures were prepared from concentrated stock solutions stored at −80° C.

Anti-Sense Sequences

DB1 is a mouse anti-sense sequence, complementary to bases 1094-1123 of the a1 connexin gene. It has four mismatches with chick a1 connexin sequence. CG1 is complementary to chick a1 connexin bases 720-749. Efficacy of this probe was improved with 1% Dimethylsulphoxide (DMSO) added to the gel. DMSO had no added effect on other anti-sense ODN or control results.

Control Sequences

DB1 (Chick) is the chick a1 connexin equivalent of DB1 matching chick a1 connexin bases 954-983. Analysis however, indicates a high probability of forming stem loop structures (G=−7.0 kcal/mol, Loop Tm=92°) and homodimerisation (Tm=1.5°) and therefore acts as a control sequence. It has been reported that some sense oligonucleotides can form stable DNA triplets (Neckers et al., 1993) inhibiting transcription. However, this was not apparent with DB1 (sense). A random control sequence with no stable secondary structure (G=1.4 kcal/mol) and unstable homodimerisation was also used, called CV3. An additional control applying equal concentration mixture of DB1 and DB1 (sense) gave background levels of defects.

Monitoring of Protein Knockdown

Immunohistochemical localisation of a1 connexin gap junction protein at cell-cell interfaces provides a direct measurement of the anti-sense effect. Antipeptide a1 connexin specific antibody probes were used to stain wholemount embryos and the connexin distribution was analysed using confocal laser scanning microscopy according to established procedures (Green et al., 1995). Control labelling for two other connexins expressed in the developing chick embryo (connexins b1 & b2) was similarly carried out, also using sequence specific antibodies (Becker et al., 1995).

Results

Reduction of a1 Connexin Expression

Using Pluronic F-127 gel to deliver unmodified a1 connexin specific antisense ODN's to the developing chick embryo, protein expression can be interfered with at chosen time points and allows the anti-sense treatment to be targeted to specific regions of a chick embryo. A droplet of gel containing the anti-sense at a relatively low concentration was placed precisely onto individual embryos. The gel sets and remains in place for at least 12 hours and thus a sustained low dose of antisense is maintained in this region. The anti-sense applications were targeted and timed to block junction formation prior to the periods of elevated expression in the limb, neural tube and face. These times were chosen to optimise the effects of the anti-sense by reducing the expression of new protein rather than being dependent upon the turnover of protein already in the membranes of the cells of the target tissue. Both DB1 and CG1 ODN's reduced expression of a1 connexin protein within two hours in the neural tube and limb bud, dramatic within 4-8 hours and persisted at 18-24 hours and 48 hours in some tissues (data not shown). No down regulation of a1 connexin protein was evident in any of the controls used. Equally, two other members of the connexin family expressed in the chick embryo, b1 connexin and b2 connexin, were unaffected by the a1 connexin specific anti-sense ODN.

Several parallel controls were run with all of the experiments. These included; DB1 sense, DB1 anti-sense and DB1 sense combined, DB1 chick (which forms stem loop structures with itself), random ODN's CV3, Pluronic gel alone, Pluronic gel with DMSO and PBS alone). None of the controls had a noticeable effect on a1 connexin protein expression.

Experiment 2

Introduction

Astrocytes constitute the most abundant cell type in the mammalian brain. They are extensively coupled to one another and to neurons through gap junctions composed predominantly of connexin 43 (Giaume and McCarthy (1996)). Following ischaemia induced or physical brain damage these channels remain open and a spreading wave of depression (initiated by raised interstitial potassium and glutamate and apoptotic signals) is propagated (Cotrina et al., (1998); Lin et al (1998)). Waves of increased cytosolic calcium and second messenger molecules such as IP3 are slowly spread via the gap junction channels to neurons beyond the core of the damaged region, resulting in lesion spread in the 24-48 hours following the insult. In this manner, undamaged neighbouring cells are destroyed (Lin et al., 1998), the so called bystander effect.

This experiment investigates the ability of the formulations of the invention to prevent this bystander effect.

Materials

Oligodeoxynucleotides were prepared with the following sequences:

```
                                         (SEQ ID NO: 2)
GTA ATT GCG GCA GGA GGA ATT GTT TCT GTC
(connexin 43)

(SEQ ID NO: 10)
TTG TGA TTT ATT TAG TTC GTC TGA TTT C (random
control)
```

Methods

Oligodeoxynucleotides (ODN's)

Oligodeoxynucleotides (ODN's)

Unmodified ODN's were delivered in Pluronic F-127 gel (BASF, Germany) in phosphate buffered saline (PBS). Pluronic gel is liquid at low temperatures (0-4° C.) and sets at physiological temperatures, and is also a mild surfactant. Unmodified ODN's normally have a half life of approximately 20 min in cells (Wagner, 1994) but the Pluronic gel loading method provides a continual diffusion source, the gel acting as a reservoir Becker et al., (1999)). ODN's specific to connexin 43 were applied, or control random ODN's of similar base composition, at 2 µM final concentration. Gel only controls were also carried out. ODN's were 30 mers analysed to show that no hairpin looping or homodimerisation should occur.

Lesioning

Brain lesions were carried out on 250-300 g male Wistar rats. Animals were anaesthetised with 1-2% halothane in oxygen and the head held in a steriotaxic clamp. The region around the lesion site was shaved and the skin over the skull slit in a sagittal plane with a scalpel and pulled back to leave the skull plates clear. A 0.5 mm diameter hole was drilled through the skull plate 3 mm to the right of bregma using an Arlec engraver and a lesion made into the cortex of the brain using a 19 G 1½ gauge syringe needle attached to a micrometer stage. The stage allowed accurate directional control and a precise 2 mm penetration depth which kept the lesion within the cortex and well above the corpus callosum.

With the animal prepared, 10 ml of ice cold Pluronic F-127 gel (BASF) containing connexin 43 specific ODN (or a control ODN) was sucked into a precooled 19 G 1½ gauge syringe needle filed off so as to have a flat tip. The syringe needle was attached to a volumetric pipette via a cut down yellow pipette tip. The gel then set in the needle as it warmed to room temperature. The needle with the gel plug at its tip was transferred to a 1 ml syringe containing PBS and a sleeve slipped over the needle shaft so that the needle tip could be lowered into the lesion with the sleeve (coming up against the skull) preventing overpenetration. Gentle pressure on the syringe plunger "popped" the gel plug out of the needle into the lesion. The wound was then treated with hydrogen peroxide to stop bleeding and the skin sutured back into place. Animals were carefully monitored and left until ready for sacrifice 24 hours, 48 hours or 12 days later.

Frozen Sectioning

Animals were sacrificed using Nembutal (pentobarbitone sodium, Virbac) and decapitated. The brains were removed intact and immediately frozen in dry ice snow and stored at −80° C. until ready for sectioning. Serial cryosections (30 mm sections) were taken from front to rear (coronal plane), the sections dry mounted onto chrome alum treated slides, and stored for histochemistry or immunohistochemistry at −80° C. The first and last section of each lesion was recorded so that the mid-point sections of the lesion were clearly identified.

Histochemistry

For haemotoxylin and eosin staining sections were hydrated through a descending series of alcohols (absolute, 2× 95%, 1× 70% and water) and stained in Gill's haemotoxylin for 4 minutes. The sections were then washed in water, dipped in Scott's water and rewashed in water. They were then stained for 30 seconds in Moore's buffered eosin. The sections were washed once more in water before dehydration through a series of alcohols (2× 95%, 1× absolute), 50:50 alcohol:xylol and dipped in xylene. The sections were then mounted using Histomountä mounting medium.

For Nissl staining, sections were dehydrated in an ascending graded series of alochols (75%, 95%, 3× 100%), five minutes in each, and defatted in xylene for five minutes. The sections were then rehydrated by descending through the same series of alcohols and washed in water. The sections were then placed in a Nissl staining solution (5 ml of a 2% aqueous Cresyl violet stock solution, 90 ml of a 6% glacial acetic acid in water solution, 10 ml of a 1.35% sodium acetate solution) for 10 minutes. The sections were then quickly dehydrated in a series of ascending alcohols for 5 minutes at 75%, then 2 minutes each at 95% and 3×100%, three charges of xylene for 10 minutes each. They were then coverslipped with Histomountä mounting medium.

Immunohistochemistry

Frozen sections were first allowed to come back up to room temperature in PBS. They were then permeabilised in methanol for two minutes, rinsed in PBS and transferred to a solution of 0.1 M lysine and 0.1% Triton-X 100 in PBS for blocking over 30 min. Two washes in PBS, each of two minutes, followed. PBS was removed and 50 ml per section of primary antibody was applied.

Immunohistochemistry was carried out with primary antibodies against connexin 43, Neuronal-Nuclei (vertebrate specific nuclear protein NeuN) and GFAP (glial fabrillary acidic protein). The following antibodies were used:

Rabbit anti-Cx 43 (Gourdie et al., (1991)) at a concentration of 1:300.
Mouse anti-Cx 43 (Chemicon International, Inc.) at a concentration of 1:100.
Rabbit anti-rat GFAP (DAKO, Z0334), at a concentration of 1:1000.
Mouse anti-Neuronal Nuclei (Chemicon International, Inc.) at a concentration 1:1000.

For connexin and GFAP labelling sections were incubated overnight at 4° C. They were then washed three times 15 minutes in PBS on an orbital shaker. Following this, excess PBS was removed and 50 ml per section of Alexaä 488 anti-rabbit IgG (Molecular Probes, Oregon, USA) was applied at a concentration of 1:200. For monoclonals and double labelling a CY3 (Chemicon, 132C) anti-mouse secondary antibody was used. Sections were incubated in the dark for two hours at room temperature followed by three washes of 15 minutes in PBS. For mounting excess PBS was removed from the slides and one or two drops of Citifluor (glycerol/PBS solution) anti-fade medium was applied. A coverslip was lowered onto the sections and sealed with nail varnish. For Neuronal-N labelling the secondary antibody was a biotinylated Goat anti-mouse followed by an avidin linked HRP and DAB reaction (Sigma ExtrAvidin or DAKO Quickstain kit).

Imaging and Analysis

Immunofluorescent labelling was carried out using a Leica TCS 4D confocal laser scanning microscope. Double labelled images were subsequently combined using the Leica Combine function or in Adobe Photoshop. Haemotoxylin and eosin, and Nissl stained samples or Neuronal-N labelled sections were captured using a Kontron (Zeiss) Progress 3008 digital camera and lesion areas analysed using MetaMorph (Universal Imaging Corp). Lesion areas were analysed for the middle section of each lesion.

Results

Figure 2A:
FIG. 2A shows Nissl staining (blue nuclei) and Neuronal-N labelling of viable neurons.
Figure 2B:
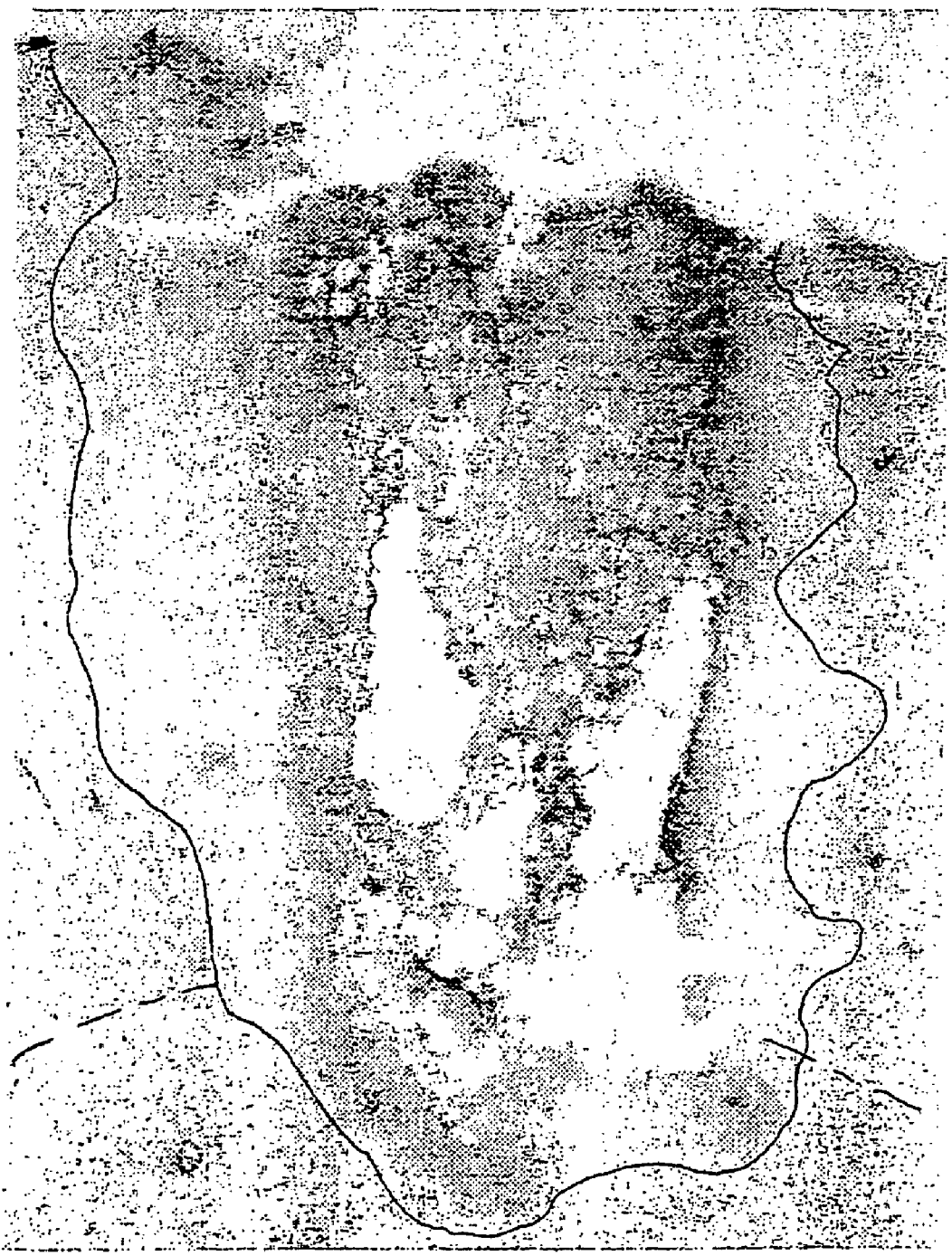
FIG. 2B is a grey scale equivalent with the lesion edge marked and the top of the corpus callosum marked (dashed line). The original needle tract is clear but neuronal death has occurred well back from the lesion edge as indicated by the Neuronal-N labelling. The edges of the lesion are irregular and the lesion, within just 24 hours, has spread right down into the corpus callosum.
Figure 3A:
FIGS. 3A and 3B are colour and grey scale images of a connexin 43 antisense treated lesion, 48 hours after lesioning. The lesion outline has been marked on FIG. 3B to show the extent of the lesion and the top of the corpus callosum marked (dashed line).
Figure 3B:
Figure 4A:
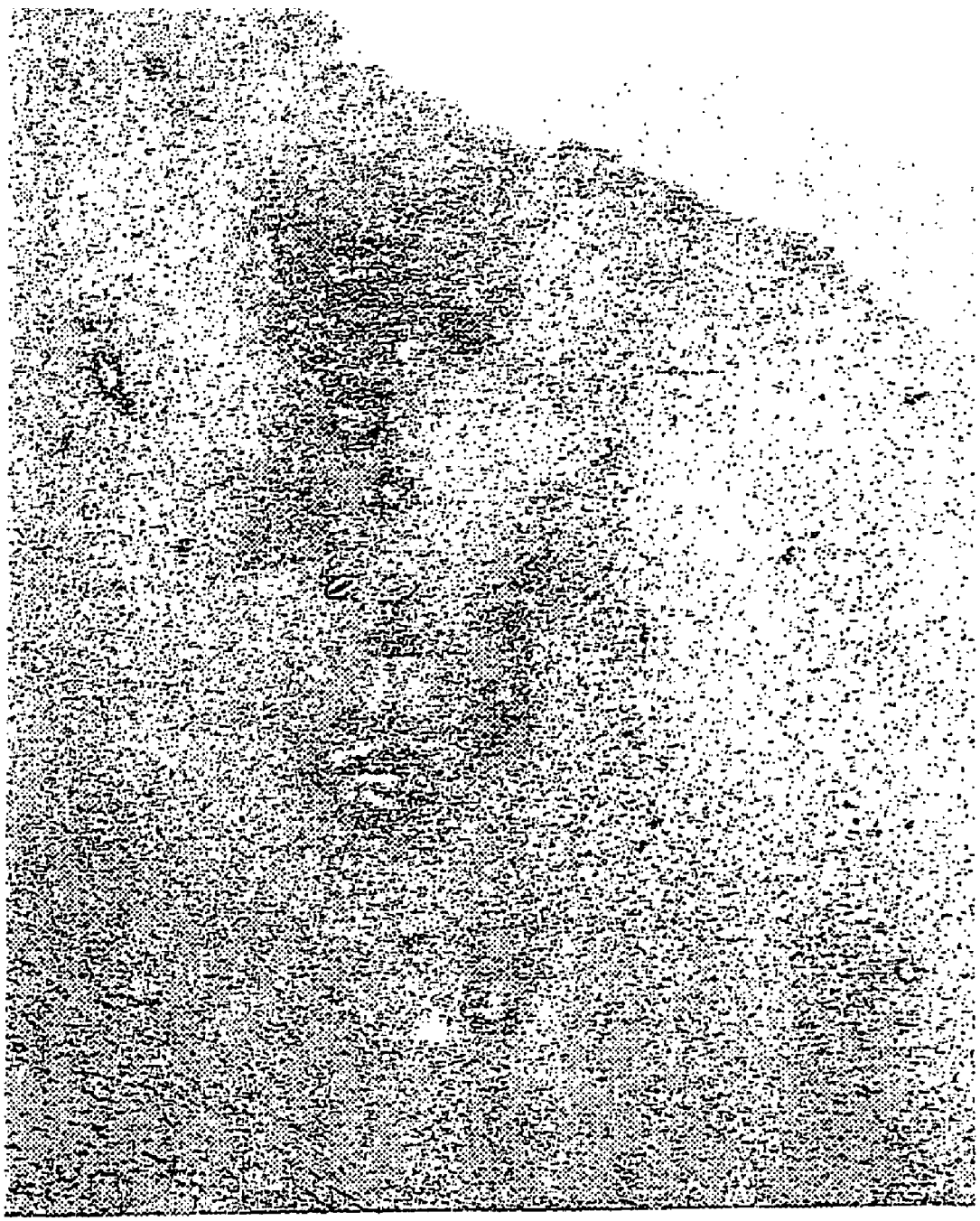
FIGS. 4A and 4B show another connexin 43 antisense treated lesion 48 hours after wounding. The labelling is the same as in FIG. 3 with the lesion outlined on the grey scale image (FIG. 4B). Even after 48 hours this lesion is extremely compact with slight spreading only to the left (medial side). Note how straight the right hand side of the lesion is with viable neurons right up to the edge of the needle tract (and indeed surviving within the lesioned area). The lesion is well above the corpus callosum (dashed line) indicating virtually no downward spread.
Figure 4B:
Figure 5:
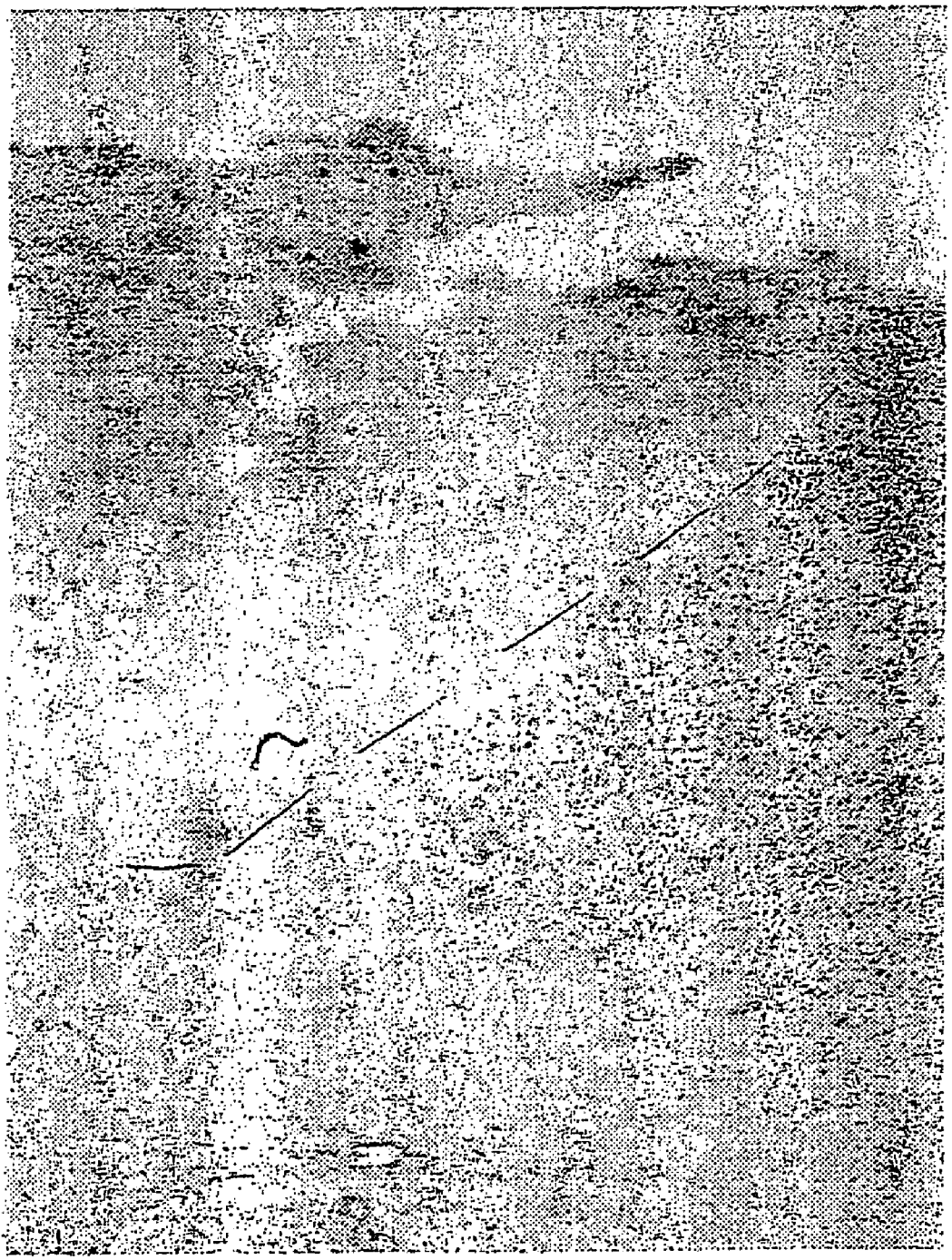

The well documented spread of brain lesions in the first 24-48 hours after trauma occurred in our control gel experiments and all lesions, controls and antisense treated, tended to spread near the outer edge where the gel is less likely to sit after loading. However, control lesions spread downwards into the corpus callosum and sideways to form ragged, spreading edges (FIGS. 1 and 2). Examination of Neuronal-N antibody labelled tissues reveals neuronal death occurring well back from the lesion edge, with areas of Nissl staining in which no viable neurons remain. This spread occurs predominantly within 24 hours (FIGS. 1 and 2), continuing up to 48 hours after lesioning. This is especially apparent in FIG. 2 where neuronal death is evident within 24 hours well back from the lesion edge into otherwise normal looking tissue, and the lesion has spread right down into the corpus callosum. In contrast, the better connexin 43 antisense treated lesions remain confined to the original lesion site and have clearly defined base levels (FIGS. 3 and 4). Neuronal N labelling colocalises with Nissl stained tissue and none of the connexin 43 antisense treated lesions spread through the corpus callosum. Neuronal-N labelling shows neuronal survival right up to the edge of the original needle tract lesion. Surviving neurons around these lesions often define sharp boundaries marking the edge of the needle tract (FIGS. 3 and 5). More tissue remains viable within the lesion itself after antisense treatment; in control lesions cell death leads to tissue loss within the lesion area (compare control lesion in FIG. 2 at 24 hours with antisense treated lesions in FIGS. 3 and 4 at 48 hours).

Figures 6, 7:
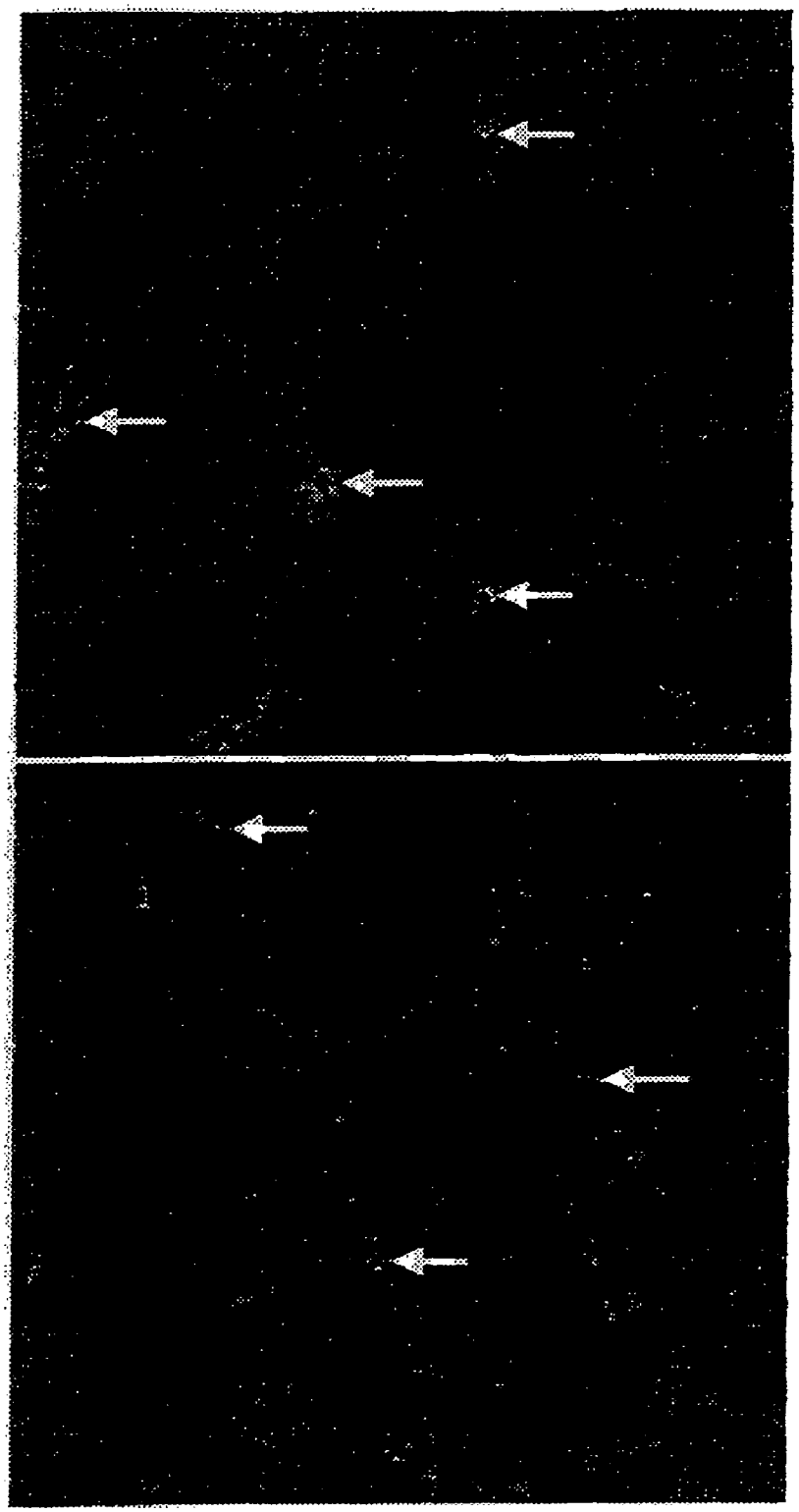
FIG. 6: GFAP (red) and connexin 43 (green) immunohistochemical labelling of a connexin 43 specific antisense treated lesion, 24 hours after lesioning. The image is taken at the lateral edge of the lesion at a point half way down the depth of the lesion. Activated astrocyte levels are elevated compared with controls (FIG. 7) and connexin 43 levels are markedly reduced. The connexin labelling remaining is generally associated with blood vessels (arrows).
FIG. 7: GFAP (red) and connexin 43 (green) immunohistochemical labelling of a control lesion, 24 hours after lesioning. The image is from the medial edge of the lesion and shows GFAP levels slightly elevated over unlesioned cortex. Note the extensive connexin 43 labelling, often co-localised with the GFAP astrocytic marker (arrows).

While antibody labelling of glial fibrillary acidic protein (GFAP) shows some increased astrocyte activation at the edges of lesions, connexin 43 protein levels are clearly reduced at many places along the edge of antisense treated lesions, particularly the basal and medial edges (FIG. 6) compared with controls (FIG. 7). In some areas the only connexin 43 labelling remaining 24 hours after connexin 43 specific antisense treatment is in blood vessel walls despite raised GFAP levels (FIG. 6). In general, connexin 43 labelling around antisense treated lesion collocalises to a much lesser extent with GFAP labelling than in controls in which over half of the connexin 43 labelling is astrocyte related. Other connexin levels (connexins 26 and 32) did not appear to be altered by the connexin 43 specific antisense treatments.

36 animals were lesioned. Cross sectional area (central slice of the lesion volume in a coronal plane) was analysed for 21 animals. The results are shown in Table 2.

TABLE 2

Cross sectional areas of lesions treated with control and connexin 43 specific oligodeoxynucleotides, left empty, or treated with gel only. Measurements are for animals measured after 24 hours, 48 hours and 12 days. Two sets of figures are included-measurements of the entire lesion, and measurements from 1 mm below the surface. In analysis of the second group the largest DB 1 treated lesion (brackets) is excluded as it falls outside 3 standard deviations from the mean for this group. Note that the rat brain does heal (unlike other species) and 12 days lesion measurements do not represent the original extend of lesion spread.

|  | 24 hours | 48 hours | 12 days |
| --- | --- | --- | --- |
| Entire Lesion: (measurements in square mm) | | | |
| DB1 | 2.42; 3.16; 3.78; 5.57 | 3.7; 6.05; 2.91; 3.41; 4.53 | 2.79; 2.86 |
| HB3 | 7.14 | 13.19 | |
| Gel/empty | 5.04: 4.48 | 3.96; 3.41; 3.56; 5.91 | 2.58; 3.3 |
| Lesions from 1 mm down: (this is considered a more accurate measure as all lesions tend to spread at the outer lip indicating that the treatment gel has settled in the bottom of the lesion and/or the outer cortex has been damaged when drilling the skull or inserting the gel loading needle. | | | |
| DB1 | 0.91; 1.13; 2.12; 2.41 | (3.38); 0.99; 1.54; 1.44; 1.08 | 0.47; 1.2 |
| HB3 | 5.9 | 5.6 | |
| Gel/empty | 3.2; 2.19 | 1.86; 1.5; 1.68; 2.17 | 1.07; 1.43 |

Figure 8:
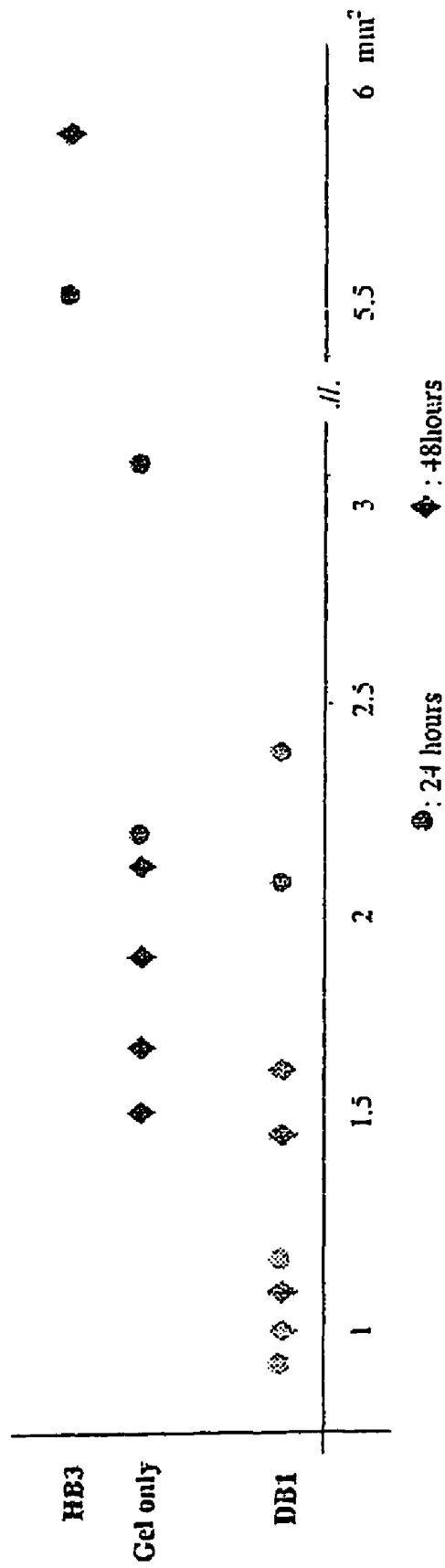
FIG. 8 shows a comparison of lesion cross sectional lower half areas 24 hours (circles) and 48 hours (diamonds) after lesioning. The analysis was carried out on a mid section of serially sectioned lesion cut on the coronal plane. Lesions were assessed using Neuronal-N antibody labelling to delineate viable neurons. DB1 treated lesions (green markers) have been treated with antisense oligodeoxynucleotides specific to connexin 43. The gel only lesion group (red markers) also includes empty lesions while the HB3 group (purple markers) are treated with gel containing random sequence control oligodeoxynucleotides. Note that while connexin 43 antisense treated lesions can be large (presumably where the antisense has not been well delivered), the smallest lesions are all connexin 43 antisense treated. Lesions were made to a depth of 2 mm and analysis covers 1 mm and below so as to exclude the outer edge where the antisense did not sit.

DB 1 is anti connexin 43 (SEQ. ID. NO: 2) treated
HB3 is random oligo (SEQ. ID. NO: 10) and appears to be toxic In the final analysis the lesion area from a line 1 mm below the outer cortex edge was measured so as to exclude lesion spread at the outer edge where antisense treatments have little or no effect (owing to gel being injected into and settling at the bottom of lesions). One antisense treated animal falls more than three standard deviations outside the mean for this group and has been excluded. Mean lesion size for antisense treated lesions at 24 and 48 hours was 1.45 mm$^2$ (+/−0.55), for controls 2.1 mm$^2$ (+/−0.6). The four smallest (of 8 antisense treated and 8 control lesions at 24 and 48 hours) were all connexin 43 antisense treated, with the smallest control lesion 50% larger than these four. This data is also shown in graphical form in FIG. 8. By 12 days regeneration occurs in the rat (but not in human brain tissue) and the limits of lesion spread are not clearly defined.

Discussion

The Pluronic gel plug-antisense ODN method has been used to study the effect of connexin 43 knockdown during astrocytosis which occurs following lesioning of the cerebral cortex of the mammalian brain. In the brain, release of toxins from dying neurons causes what is known as the bystander effect, with the toxins spreading to neighbouring cells through gap junction channels (Lin et al, (1998)). Under neurodegenerative conditions, slow release of toxins apparently leads to an upregulation of connexin 43 channels in astrocytes to enable the transport and removal of the toxins to the blood stream. In cases of severe trauma however, this upregulation aids the spread of high toxin levels to neighbouring neurons, killing them. Blocking of the connexin 43 upregulation and knockdown of connexin 43 channels prevents this spread leading to lesions up to 50% smaller in cross sectional area. This has significant implications in the management of ischeamic stroke, treatment of neurodegenerative diseases, and modulation of side effects from surgical intervention.

Experiment 3

Introduction

The bystander effect in neural tissues whereby damaged neurons release toxins which spread and kill neighbouring cells is well documented. Experiment 2 shows that this effect can be reduced in the brain using an antisense oligodeoxynucleotide sustained release approach to knockdown the gap junction protein connexin 43.

Another tissue of similar composition to the brain is the spinal cord in which the neural population is supported by populations of glial cells, including astrocytes which are responsible for the neuroprotective effect by removing glutamate and excess calcium from the neural environment. This experiment investigates the ability of the formulations of the invention to reduce the spread of spinal cord lesions.

Materials

Oligodeoxynucleotides were prepared with the following sequences:

```
                                            (SEQ ID NO: 2)
GTA ATT GCG GCA GGA GGA ATT GTT TCT GTC
(connexin 43)

(SEQ ID NO: 7)
GAC AGA AAC AAT TCC TCC TGC CGC AAT TAC (sense
control)
```

Methods

Wistar rats were anaesthetised and their spinal cord exposed. A standard hemisection lesion was then made in the cord and 5 ml of chilled Pluronic gel, containing either antisense or sense ODN's to connexin 43 (5 μM) was placed in the lesion. Applications were made blind. The exposed cord was then recovered and the rat returned to its cage. Some animals were sacrificed at 24 hours whereas others were maintained for 12 days and two months in order to determine the extent of neuronal regeneration and the final size of the lesion. For axonal regeneration studies the rats were anaesthetised and their axons severed prior to their entry site to the spinal cord. A pellet of Horse radish peroxidase (HRP) was placed in the cut in order to retrogradely label the axons over a 24 hour period. Next day the rats were sacrificed and their spinal cords removed and fixed in 2% paraformaldehyde. Cords were then processed for cryosectioning and serial longitudinal 8 mm sections were taken through the cords. Sections were then immunostained for either connexins or GFAP along with propidium iodide as a nuclear marker, or processed to reveal the HRP.

Results

Figure 9:
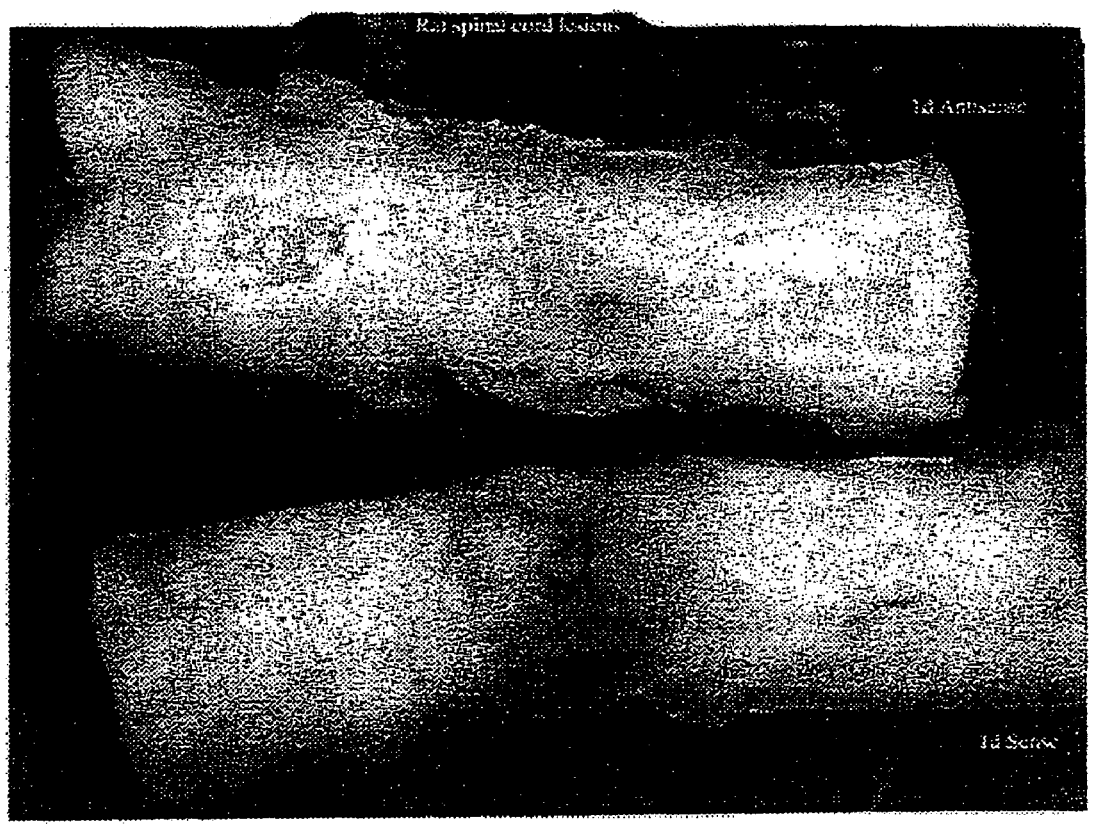
FIG. 9: Lesions in rat spinal cord 24 hours after treatment with connexin 43 sense and antisense ODN's. The sense lesions were no different from untreated controls whereas the antisense treated lesions were smaller and with reduced inflammation.

At 24 hours post lesion there was a marked difference between the spinal cord lesions treated with connexin 43 sense and antisense ODN's. The sense lesions appeared no different from untreated controls whereas the antisense treated lesions appeared smaller and less inflamed (FIG. 9).

At 12 days HRP labelled axons could be seen in both sense and antisense treated cords but in neither case did significant numbers of regenerating axons cross the lesion. However, there was a marked difference in lesion size with the antisense lesion appearing significantly smaller than the sense or untreated lesions.

Two months after lesioning the spinal cords HRP labelling of regenerating axons revealed that they had failed to cross the lesion site in both sense and antisense treatments. Lesion size was significantly smaller in antisense treated cords indicating a significant reduction in secondary neuronal cell death.

Discussion

Using the formulations of the invention, the antisense oligodeoxynucleotide knockdown of connexin 43 significantly reduces the lesion spread which occurs in the first 24-48 hours after spinal cord injury. The knockdown of connexin 43 also reduces inflammation, further aiding in the neuroprotective effect, but there was no change in the ability for neurons to grow back across the lesion site. Thus, antisense treatment with connexin 43 specific oligodeoxynucleotides cannot aid regrowth of damaged neurons, but has a significant neuroprotective effect reducing the spread of the insult.

Experiment 4

Introduction

To repair skin wounds a number of cell types, such as fibroblasts, endothelial cells and keratinocytes are activated to proliferate, migrate and lay down extracellular matrix to fill the wound.

Communication and intercellular signalling is a key feature of the wound healing process. Extracellular signalling mechanisms are thought to be the key players though it is also probable that intercellular signalling through the extensive networks of gap junction channels in the skin layers may also have a role. Calcium waves spreading away from injured cells through the epidermis may signal their damage. In normal wound healing connexin levels start to fall within 6 hours and take up to 6 days to recover. The roles that these changes play are not understood but one theory is that cells are released from their neighbours to divide rapidly, and then junctions reform to coordinate migration into and over the wound site.

This experiment investigates the ability of the formulations of the invention to effect wound healing.

Materials

Oligodeoxynucleotides were prepared with the following sequences:

```
                                           (SEQ ID NO: 2)
GTA ATT GCG GCA GGA GGA ATT GTT TCT GTC
(connexin 43)
```

```
                                           (SEQ ID NO: 7)
GAC AGA AAC AAT TCC TCC TGC CGC AAT TAC (sense
control)
```

Methods

Neonatal mice, CD1 strain, were anaesthetised with local anaesthetic by spray. A clean incision wound, 2 mm long, was then made along the length of both fore paws with an iridectomy knife. By making the wounds under a dissecting microscope they can be made very reproducible in size. They generally heal in 3-6 days. Carbon powder was dusted into the wounds in order to mark them for subsequent identification of the wound site at late time points—this does not affect the healing in any way. 5 ml of chilled Pluronic gel, containing either Sense or Antisense ODN's was then applied to the wounds. The Pluronic gel is liquid between 0-4° C. but sets at higher temperature. Once applied to the wound the gel sets in place and acts as a slow release reservoir for the ODN's as well as a mild surfactant, aiding the penetration of ODN's into the tissue. Application of Sense ODN's was made to one paw and Antisense to the other, alternating left and right between litters. Pups were warmed under a lamp and then returned to their mother. Wounds were examined daily and scored for quality of healing. Representative pups were selected at 1 day, 5 day and 8 day post operation and their forelimbs photographed before the pups were anaesthetised and perfused with 2% paraformaldehyde. The forelimbs were removed and immersion-fixed in 2% paraformaldehyde overnight and then processed for resin (1 day) or wax (2 days onward) histology.

Inflammation of the wound was assessed 24 hours after wounding. Resin sections through the wound are stained with Toluidine blue to reveal nissl positive cells, neutrophils, which are the first cells to respond to injury. These can also be revealed using neutrophil specific markers.

Cell death and clearance is assessed by Tunel labelling to determine the rate of clearance of apoptotic cells. Macrophage staining was used to show the period of clearing up following cell death. These are carried out days 3-5 post wounding.

Angiogenesis

Granulation is a feature of healing connective tissue and is cased by the invasion of numerous capillaries. Macrophages are known to express potent angiogenic factors such as VEGF. The degree of vascularisation is monitored with antibodies to VEGF receptors, anti-PCAM and anti-flt-1 which are both good blood vessel markers. Contraction of this tissue is brought about by the differentiation of wound fibroblasts into a contractile myofibroblast. After they have pulled the wound together they die apoptotically and are removed by macrophages. These cells can be revealed by smooth muscle actin specific antibodies and their formation and removal followed.

Hyperinnervation

Sensory nerves are very sensitive to the signals released on wounding and show transient sprouting at the sites of adult wounds. However, in neonatal wounds this sprouting is more profuse and results in permanent hyperinnervation. Whilst it is not clear what these signals are it is likely that they are released from inflammatory macrophages. Hyperinnervation is maximal at 7 d post wounding and nerve distribution can be revealed using PGP 9.5 antibody against neurofilaments.

Scarring is normally assessed weeks or months after closure of the wound. However, a reasonable assessment can be made 12 days after wounding. Sections through the wounds are stained with the collagen stain Picrosirus Red and examined on a confocal microscope to determine the collagen density and orientation at the wound site.

Results 1 day

Figure 10:
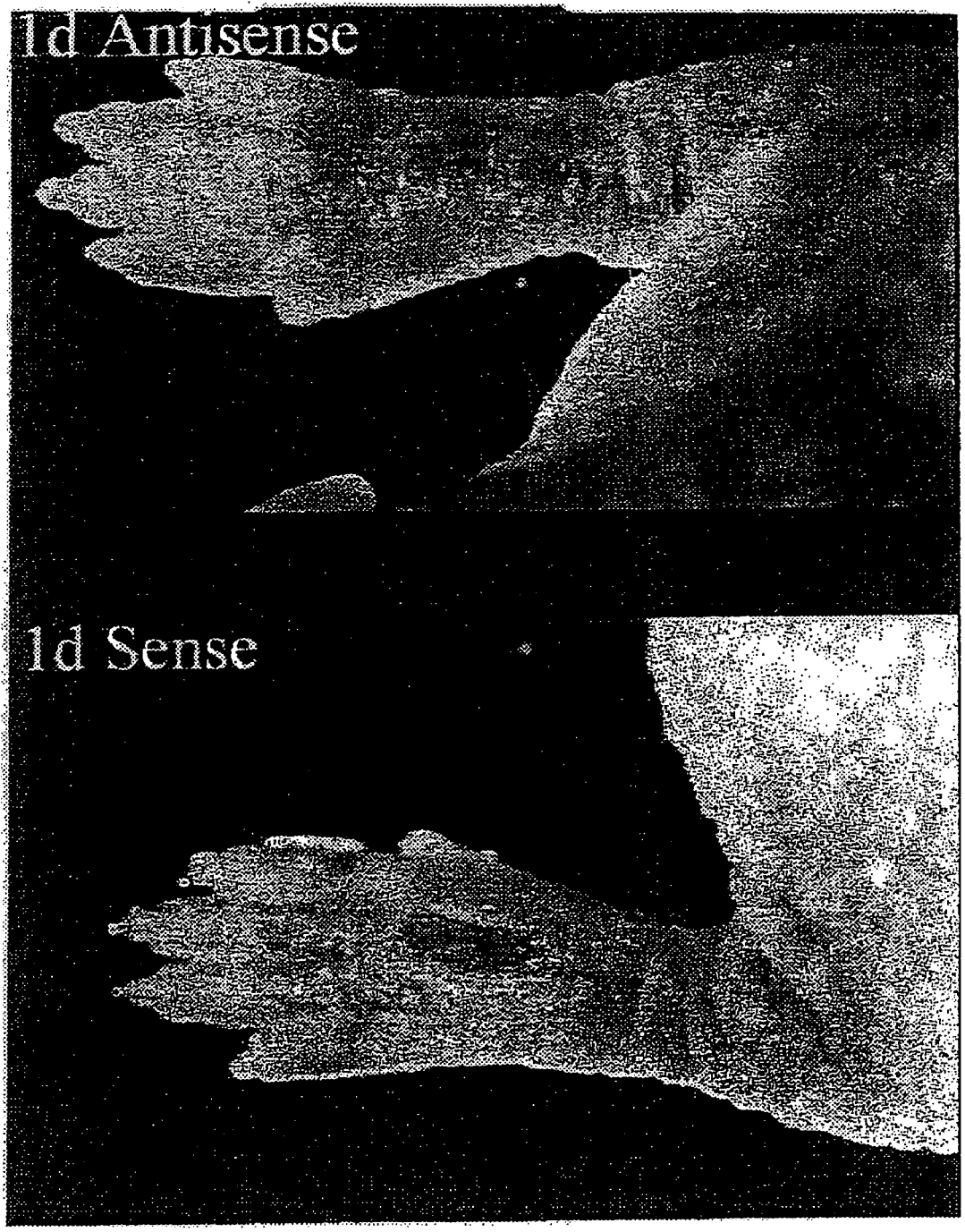
FIG. 10: Lesions in neonatal mouse fore paws 24 hours after treatment with connexin 43 sense ODNs (left paw) or antisense ODNs (right paw). Note the reduction in inflammation and increased rate of healing on the antisense treated paw.

At 24 hours after wounding marked differences were apparent between the sense and antisense treated limbs. Sense treated wounds looked no different from untreated with a normal spectrum of healing grades and rates (FIG. 10). Antisense treated limbs were markedly different from the controls, they appeared to be less inflamed and the healing rate was generally faster.

Figure 11:
FIG. 11: Sections through the centre of the 24 hour wounds shown in FIG. 10. The sections have been stained with toluidine blue to reveal neutrophils. There are significantly less neutrophils in the antisense treated wound which was also less inflamed.

Resin sections of representative limbs stained with a nissl stain revealed significantly less neutrophils cells indicating a less inflamed tissue (FIG. 11).

5 days

Figure 12:
FIG. 12: Pairs of rat paw lesions five days after lesioning that have been treated with connexin 43 specific antisense ODNs or sense control ODNs. Antisense treated lesions are healing quicker and show less signs of scarring.

By days after wounding scabs had started to fall off. At this stage most of the antisense treated wounds appeared to be smaller than the sense treated with either small scabs or less prominent scarring (FIG. 12).

Figure 13:
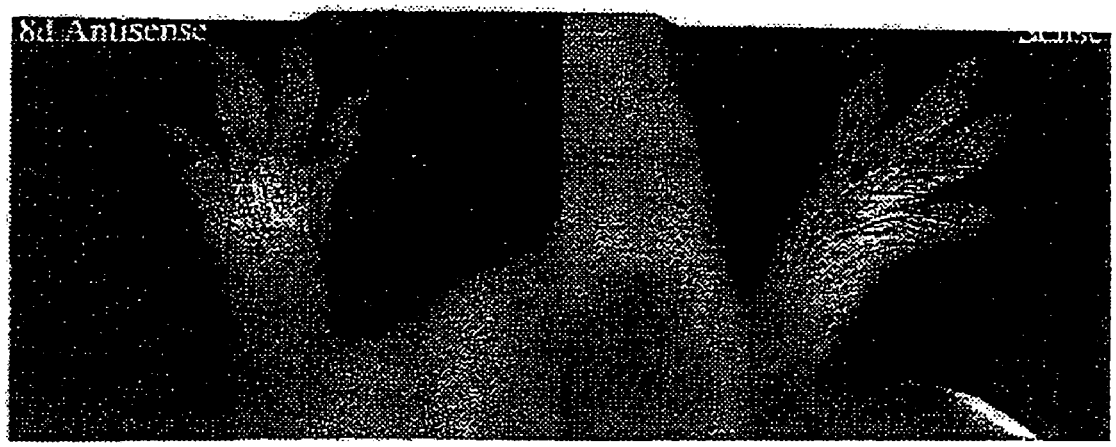
FIG. 13: Pairs of rat paw lesions made at the neonate stage, and viewed here 8 days after lesioning. Lesions were treated with connexin 43 specific antisense or control sense ODN. Hair has grown and it is clear that antisense treatment has resulted in smaller scars and less hair loss. The site of the lesion remains prominent in the sense treated control but is difficult to detect in the antisense treated limb.

8 days 8 days after wounding the limbs had grown hair. Sense treated wounds were still visible being demarcated by a lack of hair around the wound site. Antisense treated wounds were mostly invisible being covered by normal hair growth. This difference in hair growth indicates reduced scarring has occurred in the antisense treated wounds (FIG. 13).

19

Conclusions

Application of connexin 43 antisense ODN's to a wound has a marked affect on the healing process. The first noticeable effect is a reduction in the inflammation of the wounds which is noticeable in sections which show a much lower inflammatory response in terms of levels of neutrophils. As healing progresses, antisense treated wounds heal faster and with less scarring than control lesions.

This reduction in inflammatory response and subsequent improved healing is possibly owing to reduced neutrophil communication and to a speeding up of natural healing processes. The antisense ODN's can reduce connexin expression in 4-8 hours so they will not have an effect on the initial signalling of wounding but play a role in the secondary signalling events. It is interesting to note that neutrophils which invade in response to the wounding normally express large amounts of connexin 43. It is also possible that they form gap junctions with other cells in the wound and communicate with them. Reduction in this form of communication may result in a reduction of secreted factors from the neutrophils and may reduce cell death in the wound as well as granulation and hyperinnervation. It is also known that under normal conditions connexin protein levels (connexins and 43) are reduced in both the epithelial and subdermal layers of wounds starting within 6 hours, and remaining lowered for up to 6 days. The antisense approach may speed up this initial protein reduction by blocking translational processes as protein removal from the membrane is occurring. Certainly, the effects of connexin 43 knockdown immediately following wounding has marked effects on reducing inflammatory levels and increasing healing rates.

Experiment 5

Introduction

The inflammation and secondary cell death that follows burning is of major concern. Victims of severe burns over a high percentage of their body often die one or two days after trauma. This experiment investigates the ability of the formulations of the invention to beneficially affect the burn recovery process.

Materials

Oligodeoxynucleotides were prepared with the following sequences:

```
                                        (SEQ ID NO: 2)
GTA ATT GCG GCA GGA GGA ATT GTT TCT GTC.
(connexin 43)
```

```
                                        (SEQ ID NO: 7)
GAC AGA AAC AAT TCC TCC TGC CGC AAT TAC (sense
control)
```

Methods

Reproducible burns are delivered to moistened skin, and Pluronic gel containing antisense ODN's injected subdermal to the burn. A series of burns were made using a soldering iron to the left and right sides of the skull of six newborn mice. The burns on one side of the head were treated with connexin 43-specific ODN in Pluronic gel and those on the other side with sense control ODN in Pluronic gel.

Results

After 24 hours, all six connexin 43 ODN treated burns showed lower levels of inflammation compared with the control burns. These differences were marked (data not shown).

Utility

Thus, in accordance with the invention, there are provided formulations by which cell-cell communication can be downregulated in a transient and site-specific manner. The formulations therefore have application in methods of therapy and in cosmetic treatments.

The delivery of the ODN component of the formulation for an extended period (24 hours or longer) is a particular advantage in treating neuronal damage. This is because, in most instances of direct physical neuronal insult, neuronal cell loss extends well beyond the site of actual injury to the surrounding cells. This secondary neuronal cell loss occurs within 24 hours of the original injury and is mediated by junction gap cell-cell communication. Downregulation of connexin protein expression therefore blocks or at least downregulates communication between the cells and minimises secondary neuronal cell damage.

Equally, in instances of other tissue damage (particularly wounds) the formulations of the invention have been found effective in both promoting the wound healing process, reducing inflammation and in minimising scar formation. The formulations therefore have clear benefit in the treatment of wounds, whether the result of external trauma (including burns) or surgical intervention.

It will further be appreciated that the above description is provided by way of example only and that modifications can be made, both in terms of the specific ODN's and pharmaceutically acceptable carriers or vehicles employed without departing from the scope of the present invention.

TABLE 3

(SEQ ID NO: 12)

```
  1  atgggtgactggagcgcctt aggcaaactc cttgacaagg ttcaagccta ctcaactgct 61  ggagggaaggtgtggctgtc agtactttc atttccgaatcctgctgct ggggacagcg 121  gttgagtcagcctggggaga tgagcagtct gcctttcgtt gtaacactca gcaacctggt 181  tgtgaaaatg tctgctatga caagtctttcccaatctctc atgtgcgctt ctgggtcctg 241  cagatcatat ttgtgtctgt acccacactcttgtacctgg ctcatgtgttctatgtgatg 301  cgaaaggaag agaaactgaa caagaaagag gaagaactca aggttgccca aactgatggt 361  gtcaatgtgg acatgcactt gaagcagatt gagataaagaagttcaagta cggtattgaa 421  gagcatggta aggtgaaaat gcgagggggg ttgctgcgaa cctacatcat cagtatcctc 481  ttcaagtcta tctttgaggt ggccttcttg ctgatccagt ggtacatcta tggattcagc
```

TABLE 3-continued

```
 541 ttgagtgctg tttacacttg caaaagagat ccctgcccac atcaggtgga ctgtttcctc
 601 tctcgcccca cgagaaaac catcttcatc atcttcatgc tggtggtgtc cttggtgtcc
 661 ctggccttga atatcattga actcttctat gttttcttca agggcgttaa ggatcgggtt
 721 aagggaaaga gcgaccctta ccatgcgacc agtggtgcgc tgagccctgc caaagactgt
 781 gggtctcaaa aatatgctta tttcaatggc tgctcctcac caaccgctcc cctctcgcct
 841 atgtctcctc ctgggtacaa gctggttact ggcgacagaa acaattcttc ttgccgcaat
 901 tacaacaagc aagcaagtga gcaaaactgg gctaattaca gtgcagaaca aaatcgaatg
 961 gggcaggcgg gaagcaccat ctctaactcc catgcacagc cttttgattt ccccgatgat
1021 aaccagaatt ctaaaaaactagctgctgga catgaattac agccactagc cattgtggac
1081 cagcgacctt caagcagagc cagcagtcgtgccagcagca gacctcggcctgatgacctg
1141 gagatctag
```

REFERENCES

Becker, D. L., Evans, W. H., Green, C. R., Warner, A. (1995): Functional analysis of amino acid sequences in connexin 43 involved in intercellular communication through gap junctions. J. Cell Sci. 108, 1455-1467.

Becker, D. L., McGonnell, I., Makarenkova, H. P., Patel, K., Tickle, C., Lorimer, J. and Green, C. R. (1999). Roles for al connexin in morphogenesis of chick embryos revealed using a novel antisense approach. Devel. Genetics, 24, 33-42.

Cotrina, M. L., Kang, J., Lin, J. H-C., Bueno, E., Hansen, T. W., He, L., Lie, Y. and Nedergaard, M. (1998). Astrocytic gap junctions remain open during ischemic conditions. J. Neurosci., 18, 2520-2537.

Giaume, C. and McCarthy, K. D. (1996). Control of gap junctional communication in astrocytic networks. TINS, 19, 319-325.

Gourdie, R. G., Green, C. R., Severs, N. J. (1991). Gap junction distribution in adult mammalian myocardium revealed by an anti-peptide antibody and laser scanning confocal microscopy. J. Cell Sci. 99: 41-55.

Green, C. R., Bowles, L., Crawle, A., Tickle C. (1994): Expression of the connexin 43 gap junctional protein in tissues at the tip of the chick limb bud is related to epithelial-mesenchymal interactions that mediate morphogenesis. Devel. Biol., 161, 12-21.

Lin, J. H., Weigel, H., Cotrina, M. L., Liu, S., Bueno, E., Hansen, A. J., Hansen, T. W., Goldman, S. and Nedergaard, M. (1998). Gap-junction-mediated propogation and amplification of cell injury. Nature Neurosci., 1, 431-432.

Neckers, L., Whitesell, L. (1993): Anti-sense technology: biological utility and practical considerations. Am. J. Physiol. 265 (lung cell mol physiol), LI-LI2.

Simons, M., Edelman, E. R., DeKeyser, J. L., Langer, R., Rosenberg, R. D. (1992): Anti-sense c-myb oligonucleotides inhibit intimal arterial smooth muscle cell accumulation in vivo. Nature, 359, 67-70.

Stein, C. A. (1992): Anti-sense oligodeoxynucleotides-promises and pitfalls, Leukemia 6, 967-974.

Wagner, R. W. (1994): Gene inhibition using anti-sense oligodeoxynucleotides, Nature, 372, 333-335.

The invention claimed is:

1. A method of decreasing lesion spread in tissue of a subject which comprises administering to the tissue an amount of a connexin 43 antisense polynucleotide effective to decrease lesion spread.

2. A method according to claim 1 wherein the tissue is neural tissue.

3. A method according to claim 1 wherein said neural tissue is brain, spinal cord or optic nerve.

4. A method according to claim 1 wherein the tissue is skin.

5. A method according to claim 1 wherein the tissue is or has been wounded or subjected to physical trauma.

6. A method according to claim 5 wherein the wound or physical trauma is a burn.

7. A method according to claim 5 wherein the wound or physical trauma is an incision or due to an incision.

8. A method according to claim 5 wherein the wound or physical trauma is due to surgery.

9. A method according to claim 8 wherein the wound or physical trauma is an incision.

10. A method according to claim 5 wherein said trauma is caused by or is a result of surgery, a wound or an ischemic stroke.

11. A method according to claim 10 wherein said tissue is neural tissue which is selected from the group consisting of brain and spinal cord.

12. A method according to claim 1 wherein lesion spread is caused by or is a result of a neurodegenerative disease.

13. A method according to claim 1 wherein said polynucleotide is an oligodeoxynucleotide.

14. A method according to claim 1 wherein said polynucleotide has from about 6 to 40 nucleotides.

15. A method according to claim 14 wherein said polynucleotide has about 30 nucleotides.

16. A method according to claim 14 wherein said polynucleotide comprises one of SEQ ID NOS:1 to 3.

17. A method according to claim 14 wherein said polynucleotide comprises SEQ ID NO:2.

18. A method according to claim 17 wherein said polynucleotide is an unmodified phosphodiester oligomer.

19. A method according to claim 17 wherein said polynucleotide is chemically modified.

20. A method according to claim 17 wherein said polynucleotide is a mixed backbone oligonucleotide.

21. A method according to claim 14 wherein said connexin 43 antisense polynucleotide has at least about 70 percent homology to an antisense sequence of connexin 43 mRNA.

22. A method according to claim 21 wherein said polynucleotide has at least about 80 percent homology.

23. A method according to claim 21 wherein said polynucleotide has at least about 90 percent homology.

24. A method according to claim 21 wherein said polynucleotide has at least about 95 percent homology.

25. A method according to claim 21 wherein said polynucleotide has at least about 97 percent homology.

26. A method according to claim 14 wherein said connexin antisense polynucleotide has at least about 70 percent homology with SEQ ID NO: 2.

27. A method according to claim 26 wherein said polynucleotide has at least about 80 percent homology.

28. A method according to claim 26 wherein said polynucleotide has at least about 90 percent homology.

29. A method according to claim 26 wherein said polynucleotide has at least about 95 percent homology.

30. A method according to claim 26 wherein said polynucleotide has at least about 97 percent homology.

31. A method according to claim 14 wherein said connexin 43 antisense polynucleotide is sufficiently complementary to the connexin 43 mRNA to form a duplex having a melting point of greater than 20° C. under physiological conditions.

32. A method according to claim 31 wherein said duplex has a melting point of greater than 30° C.

33. A method according to claim 31 wherein said duplex has a melting point of greater than 40° C.

34. A method according to claim 14 wherein said connexin 43 antisense polynucleotide hybridizes to connexin 43 mRNA under conditions of the medium to high stringency.

35. A method according to claim 14 wherein said connexin 43 antisense polynucleotide hybridizes to connexin mRNA under conditions of medium to high stringency which comprise 0.03M sodium chloride and 0.03M sodium citrate at from about 50° C. to about 60° C.

36. A method according to claim 1 wherein said antisense polynucleotide is administered as a sustained release formulation.

37. A method according to claim 36 wherein said formulation is administered in an amount effective to downregulate connexin 43 protein for at least 24 hours post-administration.

38. A method according to claim 36 wherein said formulation provides sustained release of the antisense polynucleotide over at least 24 hours.

39. A method of decreasing secondary cell death in a tissue of a human subject which comprises administering to the tissue an amount of a connexin 43 antisense polynucleotide effective to decrease secondary cell death.

40. A method according to claim 39 wherein the cell death is neuronal cell death.

41. A method according to claim 40 wherein the tissue is neural tissue.

42. A method according to claim 41 wherein said neural tissue is brain, spinal cord or optic nerve.

43. A method according to claim 39 wherein the tissue is or has been wounded or subjected to physical trauma.

44. A method according to claim 43 wherein the wound or physical trauma is a burn.

45. A method according to claim 43 wherein the wound or physical trauma is due to surgery.

46. A method according to claim 45 wherein said wound or physical trauma is an incision.

47. A method according to claim 43 wherein said wound or physical trauma is caused by or is a result of an ischemic stroke.

48. A method according to claim 39 wherein the tissue is or has been subjected to physical trauma.

49. A method according to claim 48 wherein said trauma is caused by or is a result of surgery, a wound or an ischemic stroke.

50. A method according to claim 49 wherein said tissue is brain or spinal cord.

51. A method according to claim 43 where said tissue is spinal cord.

52. A method according to claim 51 wherein said connexin 43 antisense polynucleotide is administered within about 48 hours after physical trauma.

53. A method according to claim 51 wherein said connexin 43 antisense polynucleotide is administered within about 12 hours after physical trauma.

54. A method according to claim 39 wherein said polynucleotide is an oligodeoxynucleotide.

55. A method according to claim 39 wherein said polynucleotide has from about 6 to 40 nucleotides.

56. A method according to claim 55 wherein said polynucleotide has about 30 nucleotides.

57. A method according to claim 55 wherein said polynucleotide comprises one of SEQ ID NOS:1 to 3.

58. A method according to claim 55 wherein said polynucleotide comprises SEQ ID NO:2.

59. A method according to claim 58 wherein said polynucleotide is an unmodified phosphodiester oligomer.

60. A method according to claim 58 wherein said polynucleotide is chemically modified.

61. A method according to claim 58 wherein said polynucleotide is a mixed backbone oligonucleotide.

62. A method according to claim 55 wherein said connexin 43 antisense polynucleotide has at least about 70 percent homology to an antisense sequence of human connexin 43 mRNA.

63. A method according to claim 62 wherein said polynucleotide has at least about 80 percent homology.

64. A method according to claim 62 wherein said polynucleotide has at least about 90 percent homology.

65. A method according to claim 62 wherein said polynucleotide has at least about 95 percent homology.

66. A method according to claim 62 wherein said polynucelotide has at least about 97 percent homology.

67. A method according to claim 55 wherein said connexin antisense polynucleotide has at least about 70 percent homology with SEQ ID NO: 2.

68. A method according to claim 67 wherein said polynucleotide has at least about 80 percent homology.

69. A method according to claim 67 wherein said polynucleotide has at least about 90 percent homology.

70. A method according to claim 67 wherein said polynucleotide has at least about 95 percent homology.

71. A method according to claim 67 wherein said polynucelotide has at least about 97 percent homology.

72. A method according to claim 55 wherein said connexin 43 antisense polynucleotide is sufficiently complementary to the connexin 43 mRNA to form a duplex having a melting point of greater than 20° C. under physiological conditions.

73. A method according to claim 72 wherein said duplex has a melting point of greater than 30° C.

74. A method according to claim 72 wherein said duplex has a melting point of greater than 40° C.

75. A method according to claim 55 wherein said connexin 43 antisense polynucleotide hybridizes to connexin 43 mRNA under conditions of the medium to high stringency.

76. A method according to claim 55 wherein said connexin 43 antisense polynucleotide hybridizes to connexin mRNA under conditions of medium to high stringency which comprise 0.03M sodium chloride and 0.03M sodium citrate at from about 50° C. to about 60° C.

77. A method according to claim 39 where said connexin 43 antisense polynucleotide is administered in a sustained release formula.

78. A method according to claim 77 where said antisense connexin 43 polynucleotide is administered in an amount effective to down regulate connexin 43 protein for at least 24 hours post-administration.

79. A method according to claim 77 wherein said formulation provides sustained release of antisense polynucleotide over at least 24 hours.

80. A method of decreasing lesion size in tissue of a human which comprises administering to the tissue an effective amount of connexin 43 antisense polynucleotide effective to decrease lesion size.

81. A method according to claim 80 wherein the tissue is neural tissue.

82. A method according to claim 81 wherein said neural tissue is brain, spinal cord or optic nerve.

83. A method according to claim 80 wherein said tissue is skin.

84. A method according to claim 80 wherein the tissue is or has been wounded or subjected to physical trauma.

85. A method according to claim 84 wherein the wound or physical trauma is a burn.

86. A method according to claim 84 wherein the wound or physical trauma is an incision or due to an incision.

87. A method according to claim 84 wherein the wound or physical trauma is due to surgery.

88. A method according to claim 80 wherein the tissue is or has been subjected to physical trauma.

89. A method according to claim 88 wherein said tissue is neural tissue and said wound or physical trauma is caused by or is a result of surgery, a wound or an ischemic stroke.

90. A method according to claim 89 wherein said neural tissue is brain or spinal cord.

91. A method according to claim 80 wherein said polynucleotide is an oligodeoxynucleotide.

92. A method according to claim 80 wherein said polynucleotide has from about 6 to 40 nucleotides.

93. A method according to claim 92 wherein said polynucleotide has about 30 nucleotides.

94. A method according to claim 92 wherein said polynucleotide comprises one of SEQ ID NOS:1 to 3.

95. A method according to claim 92 wherein said polynucleotide comprises SEQ ID NO:2.

96. A method according to claim 92 wherein said polynucleotide is an unmodified phosphodiester oligomer.

97. A method according to claim 95 wherein said polynucleotide is chemically modified.

98. A method according to claim 95 wherein said polynucleotide is a mixed backbone oligonucleotide.

99. A method according to claim 92 wherein said connexin 43 antisense polynucleotide has at least about 70 percent homology to an antisense sequence of connexin 43 mRNA.

100. A method according to claim 99 wherein said polynucleotide has at least about 80 percent homology.

101. A method according to claim 99 wherein said polynucleotide has at least about 90 percent homology.

102. A method according to claim 99 wherein said polynucleotide has at least about 95 percent homology.

103. A method according to claim 99 wherein said polynucelotide has at least about 97 percent homology.

104. A method according to claim 92 wherein said connexin antisense polynucleotide has at least about 70 percent homology with SEQ ID NO:2.

105. A method according to claim 104 wherein said polynucleotide has at least about 80 percent homology.

106. A method according to claim 104 wherein said polynucleotide has at least about 90 percent homology.

107. A method according to claim 104 wherein said polynucleotide has at least about 95 percent homology.

108. A method according to claim 104 wherein said polynucelotide has at least about 97 percent homology.

109. A method according to claim 92 wherein said connexin 43 antisense polynucleotide is sufficiently complementary to the connexin 43 mRNA to form a duplex having a melting point of greater than 20° C. under physiological conditions.

110. A method according to claim 109 wherein said duplex has a melting point of greater than 30° C.

111. A method according to claim 109 wherein said duplex has a melting point of greater than 40° C.

112. A method according to claim 92 wherein said connexin 43 antisense polynucleotide hybridizes to connexin 43 mRNA under conditions of the medium to high stringency.

113. A method according to claim 92 wherein said connexin 43 antisense polynucleotide hybridizes to connexin mRNA under conditions of medium to high stringency which comprise 0.03M sodium chloride and 0.03M sodium citrate at from about 50° C. to about 60° C.

114. A method according to claim 80 wherein said antisense polynucleotide is administered as a sustained release formulation.

115. A method according to claim 114 wherein said formulation is administered in an amount effective to downregulate connexin 43 protein for at least 24 hours post-administration.

116. A method according to claim 114 wherein said formulation provides sustained release of the antisense polynucleotide over at least 24 hours.

117. A method of decreasing inflammation in a tissue which comprises administering to said subject tissue an amount of a connexin 43 antisense polynucleotide effective to decrease inflammation.

118. A method according to claim 117 wherein said tissue is neural tissue.

119. A method according to claim 117 wherein said neural tissue is brain, spinal cord or optic nerve.

120. A method according to claim 117 wherein said tissue is skin.

121. A method according to claim 117 wherein the tissue is or has been wounded or subjected to physical trauma.

122. A method according to claim 121 wherein the wound or physical trauma is a burn.

123. A method according to claim 121 wherein the wound or physical trauma is an incision.

124. A method according to claim 121 wherein the wound or physical trauma is due to surgery.

125. A method according to claim 121 wherein said tissue is neural tissue and the wound or physical trauma is caused by or is a result of surgery, a wound or an ischemic stroke.

126. A method according to claim 125 wherein said neural tissue is brain or spinal cord.

127. A method according to claim 117 wherein said polynucleotide is an oligodeoxynucleotide.

128. A method according to claim 117 wherein said polynucleotide has from about 6 to 40 nucleotides.

129. A method according to claim 128 wherein said polynucleotide has about 30 nucleotides.

130. A method according to claim 128 wherein said polynucleotide comprises one of SEQ ID NOS:1 to 3.

131. A method according to claim 128 wherein said polynucleotide comprises SEQ ID NO:2.

132. A method according to claim 131 wherein said polynucleotide is an unmodified phosphodiester oligomer.

133. A method according to claim 131 wherein said polynucleotide is chemically modified.

134. A method according to claim 131 wherein said polynucleotide is a mixed backbone oligonucleotide.

135. A method according to claim 128 wherein said connexin 43 antisense polynucleotide has at least about 70 percent homology to an antisense sequence of human connexin 43 mRNA.

136. A method according to claim 135 wherein said polynucleotide has at least about 80 percent homology.

137. A method according to claim 135 wherein said polynucleotide has at least about 90 percent homology.

138. A method according to claim 135 wherein said polynucleotide has at least about 95 percent homology.

139. A method according to claim 135 wherein said polynucelotide has at least about 97 percent homology.

140. A method according to claim 128 wherein said connexin antisense polynucleotide has at least about 70 percent homology with SEQ ID NO: 2.

141. A method according to claim 140 wherein said polynucleotide has at least about 80 percent homology.

142. A method according to claim 140 wherein said polynucleotide has at least about 90 percent homology.

143. A method according to claim 140 wherein said polynucleotide has at least about 95 percent homology.

144. A method according to claim 140 wherein said polynucelotide has at least about 97 percent homology.

145. A method according to claim 117 wherein said connexin 43 antisense polynucleotide is sufficiently complementary to the connexin 43 mRNA to form a duplex having a melting point of greater than 20° C. under physiological conditions.

146. A method according to claim 145 wherein said duplex has a melting point of greater than 30° C.

147. A method according to claim 145 wherein said duplex has a melting point of greater than 40° C.

148. A method according to claim 117 wherein said connexin 43 antisense polynucleotide hybridizes to connexin 43 mRNA under conditions of the medium to high stringency.

149. A method according to claim 117 wherein said connexin 43 antisense polynucleotide hybridizes to connexin mRNA under conditions of medium to high stringency which comprise 0.03M sodium chloride and 0.03M sodium citrate at from about 50° C. to about 60° C.

150. A method according to claim 117 wherein said antisense polynucleotide is administered as a sustained release formulation.

151. A method according to claim 150 wherein said formulation is administered in an amount effective to downregulate connexin 43 protein for at least 24 hours post-administration.

152. A method according to claim 150 wherein said formulation provides sustained release of the antisense polynucleotide over at least 24 hours.

153. A method according to any of claims 1, 39, 80 or 117 wherein said polynucleotide is applied in a topical formulation.

* * * * *

UNITED STATES PATENT AND TRADEMARK OFFICE
CERTIFICATE OF CORRECTION

| | | |
|---|---|---|
| PATENT NO. | : 7,879,811 B2 | |
| APPLICATION NO. | : 11/510498 | |
| DATED | : February 1, 2011 | |
| INVENTOR(S) | : Green et al. | |

It is certified that error appears in the above-identified patent and that said Letters Patent is hereby corrected as shown below:

On the Title Page, Item (75), Inventor name Richard Colin Green, Auckland (NZ) should be replaced with Colin Richard Green, Auckland (NZ)

Signed and Sealed this
Twenty-second Day of March, 2011

David J. Kappos
*Director of the United States Patent and Trademark Office*